(12) United States Patent
Vasta et al.

(10) Patent No.: US 8,377,060 B2
(45) Date of Patent: Feb. 19, 2013

(54) FIXATION DEVICE AND MULTIPLE-AXIS JOINT FOR A FIXATION DEVICE

(75) Inventors: Paul Vasta, McKinney, TX (US);
Miguel Franco, Addison, TX (US);
Michael Thomas, Van Alstyne, TX (US)

(73) Assignee: AMEI Technologies, Inc., Wilmington, DE (US)

( * ) Notice: Subject to any disclaimer, the term of this patent is extended or adjusted under 35 U.S.C. 154(b) by 329 days.

(21) Appl. No.: 12/618,498

(22) Filed: Nov. 13, 2009

(65) Prior Publication Data

US 2011/0118737 A1     May 19, 2011

(51) Int. Cl.
*A61B 17/00* (2006.01)
(52) U.S. Cl. .......................................... 606/56
(58) Field of Classification Search ................ 606/53–59
See application file for complete search history.

(56) References Cited

U.S. PATENT DOCUMENTS

| | | | |
|---|---|---|---|
| 4,365,624 A | 12/1982 | Jaquet | |
| 4,988,244 A | 1/1991 | Sheldon et al. | |
| 5,095,919 A | 3/1992 | Monticelli et al. | |
| 5,533,418 A | 7/1996 | Wu et al. | |
| 5,776,132 A | 7/1998 | Blyakher | |
| 5,891,143 A | 4/1999 | Taylor et al. | |
| 6,030,386 A | 2/2000 | Taylor et al. | |
| 2002/0010465 A1* | 1/2002 | Koo et al. | ........................ 606/57 |
| 2005/0215997 A1 | 9/2005 | Austin et al. | |
| 2007/0055234 A1 | 3/2007 | McGrath et al. | |
| 2009/0036890 A1 | 2/2009 | Karidis | |

OTHER PUBLICATIONS

International Search Report of corresponding international application No. PCT/US10/56541 dated Jan. 12, 2011.
International Preliminary Report on Patentability, PCT/US2010/056541, Date of issuance May 15, 2012, 7 pages.
International Preliminary Report on Patentability, PCT/US2010/056539, Date of issuance May 15, 2012, 9 pages.

* cited by examiner

*Primary Examiner* — Eduardo C Robert
*Assistant Examiner* — Tara Carter
(74) *Attorney, Agent, or Firm* — Baker & McKenzie LLP

(57) ABSTRACT

A fixator system includes an active strut that that can be gradually or acutely adjusted. Adjustments can be made in six degrees of freedom. Embodiments of the active strut can provide for two of the six degrees of freedom being about a first common point of rotation, and another two of the six degrees of freedom being about a second common point of rotation. Embodiments of the fixator can include one or more active struts in combination with one or more passive struts. The passive struts can be rigidly locked or can be unlocked so as to be freely and acutely adjustable while gradual or acute adjustments are made using the one or more active struts.

23 Claims, 17 Drawing Sheets

FIXATION DEVICE AND MULTIPLE-AXIS JOINT FOR A FIXATION DEVICE

TECHNICAL FIELD

The present disclosure relates in general to medical device technology, and more specifically to external fixation devices and to drive systems that allow precise control for positioning and locking such fixation devices.

BACKGROUND

Without limiting the scope of the present disclosure, its background is described in connection with external fixation devices. Generally, external fixation devices are commonly used on both the upper and lower limbs for both adults and children in a variety of surgical procedures including limb lengthening, deformity correction and treatment of fractures, mal-unions, non-unions and bone defects.

One common external fixation device is known as the Ilizarov Apparatus. The Ilizarov external fixation procedure involves a rigid framework consisting of several rings or arches that are placed externally around the limb and attached to injured (e.g., due to fracture) or surgically separated (e.g., for limb lengthening and deformity correction) bone segments using special bone fasteners (wires and pins) inserted into the bone segment and connected to the related section of the external rigid framework. The opposite rings of the rigid framework are connected by either threaded or telescopic connection rods or by assembled uni-planar or multi-planar angular hinges, which allow the surgeon to adjust the relative position of the rings to each other longitudinally or angularly over a period of time. This allows new bone to gradually form in the gap between bone segments created by this distraction technique. Once the desired position of bone segments is achieved over the course of time (e.g., 2-6 weeks), the external apparatus is stabilized into a fixed position and left on the bone segments until the fracture is healed or newly formed bone is completely or substantially mineralized, which could take up to an additional 3-6 months, depending on the nature of pathology and degree of deformity.

Another common external fixation device is a Taylor Spatial Frame as described in U.S. Pat. Nos. 6,030,386, 5,891,143, and 5,776,132. The Taylor Spatial Frame is a hexapod type of device based on a Stewart platform but shares many components and features of the Ilizarov apparatus. The Taylor Spatial Frame consists of two external fixator rings attached to bone segments by wires or half pins and connected together by six struts that may be lengthened or shortened as necessary. Adjustment of strut lengths allows manipulation of the bone segments in 6 axes (e.g., lengthening/shortening, external/internal rotation, anterior/posterior horizontal translation, medial/lateral horizontal translation, anterior/posterior angular translation, and medial/lateral angular translation) to correct linear, angular and rotational deformities simultaneously.

The fixation device would usually be placed on the affected patient by medical personnel in such a way as to align the affected body part during the healing process, holding the affected body part in the proper position for treatment. Since applications of such devices can include a wide variety of deformities, body sites, and surgical implementations, there is a need for fixation devices that can initially be acutely adjusted in order to accommodate such variabilities and subsequently maintain the affected body part in one desirable position. Moreover, a typical treatment regimen requires frequent adjustments to be performed by the patient and/or during repeated visits to medical professionals so that the fixation device could be periodically and gradually adjusted, providing the desired orientation to the affected body part and setting the proper amount of stretching and support for healing. Accordingly, there is also a need for fixation devices that allow for gradual adjustments after the fractured body part is substantially maintained in one position.

Thus, there is a need for an improved fixation device that will allow medical professionals to make effective, calibrated adjustments to the positioning of the injured body part.

BRIEF DESCRIPTION OF THE DRAWINGS

For a more complete understanding of the features and advantages of the present disclosure, reference is now made to the detailed description along with the accompanying figures and in which.

DETAILED DESCRIPTION

While the making and using of various embodiments of the multiple-axis joint according to the present disclosure are discussed in detail below, it should be appreciated that the present application provides many applicable inventive concepts that can be embodied in a wide variety of specific contexts. Without limiting the scope of the present disclosure, the multiple-axis joint is described in connection with external fixation devices. However, the multiple-axis joint can be used with other devices. The specific embodiments discussed herein are merely illustrative of specific ways to make and use the multiple-axis joint disclosed herein and do not delimit the scope of the application, and their usage does not delimit the application, except as outlined in the claims.

Figure 1:
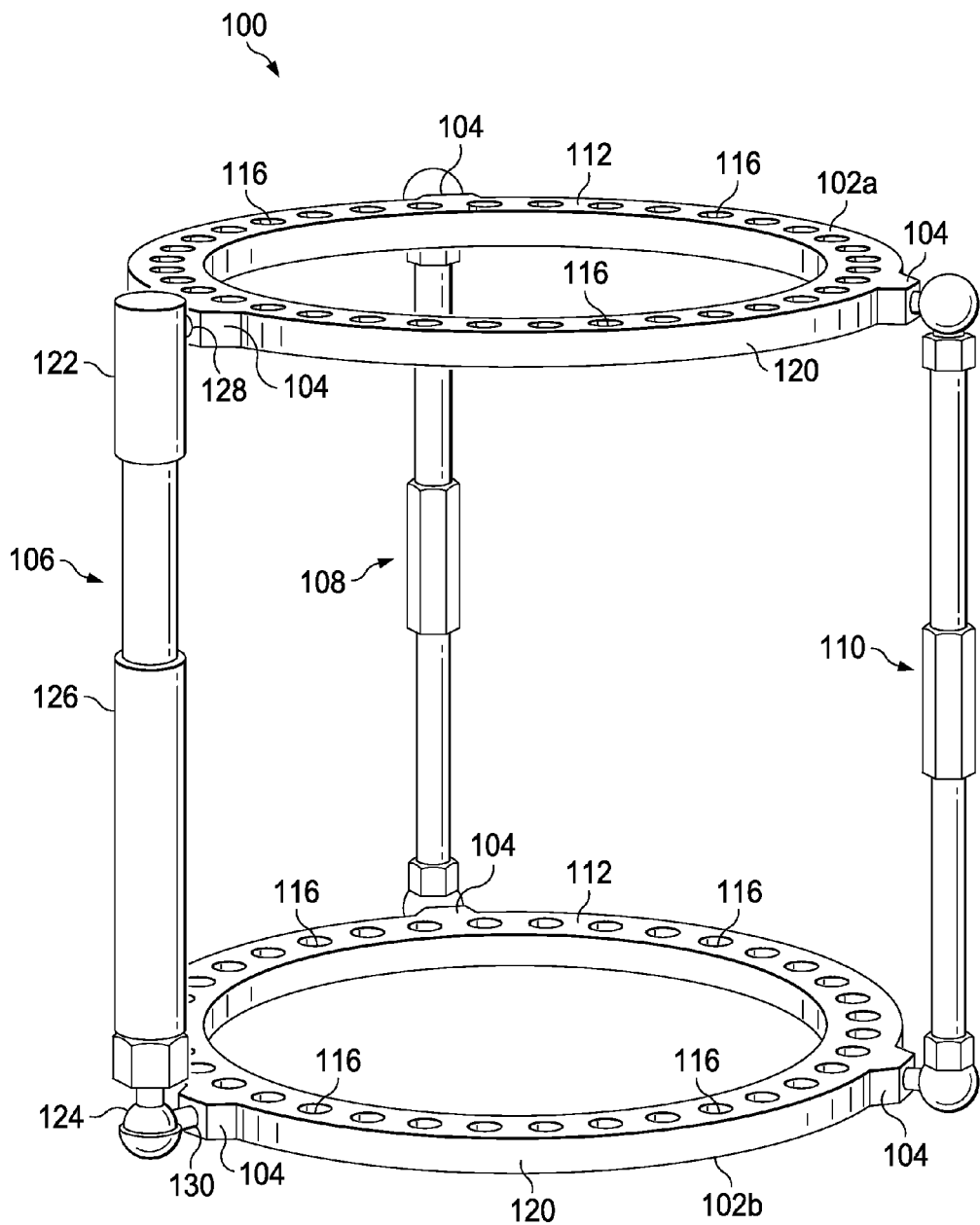
FIG. 1 is a perspective view of an external fixator ring system according to one embodiment of the present disclosure that includes an active strut in combination with a plurality of passive struts.

FIG. 1 is a perspective view of an external fixator ring system 100. The fixator ring system 100 includes a first fixator ring 102a and a second fixator ring 102b, which serve as examples of fixator base elements. The fixator rings 102a and 102b both include a plurality of strut mounting positions 104. The fixator rings 102a and 102b are connected by a plurality of connection struts 106, 108, and 110, which are attached to the fixator rings 102a and 102b at the strut mounting positions 104.

Strut 106 is an active strut, whereas struts 108 and 110 are passive struts. All of the struts 106, 108, and 110 are preferably capable of being locked into a rigid state such that the rings 102a and 102b are fixed relative to each other, and unlocked into a free state such that acute adjustments can be made to the relative positions of the rings 102a and 102b. Such acute adjustments are desirable at certain times, for example during the initial placement of the fixator ring system 100 onto an injured limb. The passive struts 108 and 110 are limited to being either locked into a passive locked state, which is a non-adjustable rigid state, or being unlocked into a freely adjustable state. The active strut 106 is capable of being locked into an active locked state, which is a rigid and adjustable state, or being unlocked into a freely adjustable state. In some embodiments, the active strut 106 can further be locked into a passive locked state so that it is even locked from being adjustable. Thus, the active strut 106 differs from the passive struts 108 and 110 in that the active strut 106 is configured for an active locked state wherein the active strut 106 is capable of being controllably articulated for making fine or gradual adjustments to the relative positions of the rings 102a and 102b with little or no loss in rigidity while such adjustments are made. Such fine or gradual adjustments between the rings 102a and 102b are desirable after the initial placement of the fixator ring system 100, for example as part of a treatment plan for an injured limb that might require periodic gradual adjustments. Thus, the fixator ring system 100 disclosed herein includes a combination of active and passive struts 106, 108, and 110. While the fixator ring system 100 includes one active strut 106 and two passive struts 108 and 110, alternative embodiments, including those described herein, can include more than one active strut and more or fewer than two passive struts.

The first fixator ring 102a includes a top surface 112 and an opposing bottom surface (not shown). The top surface 112 includes numerous holes 116 that extend through the top surface 112 to the bottom surface (not shown). The holes 116 may be used for attachment of wire and half-pin fixation elements (bolts), threaded or telescopic connection rods, plates, posts or other device connection elements to the first fixator ring 102a. In some embodiments, the outer side surface 120 of the first fixator ring 102a can include numerous threaded apertures (not shown) that provide additional attachment points for struts or other connection elements (not shown). The second fixator ring 102b can be identical or similar to the first fixator ring 102a.

Although the shape of the fixator rings 102a and 102b as shown FIG. 1 is substantially circular, the shape of the fixator rings 102a and 102b can vary to accommodate the physical contour of various body parts to which the fixation system 100 would be attached. For example, the fixator rings 102a and 102b can be fixator base elements that are configured to have an oval shape, D-shape, U-shape, C-shape, a polygon, or other irregular shapes. In some exemplary embodiments, an elliptical fixator ring (not shown) may be particularly advantageous. The insertion of pins or wires into a patient's limb can cause the surrounding tissue to swell unevenly, and in such a case, an elliptical fixator ring can accommodate the uneven swelling better than a circular ring can. The fixator rings 102a and 102b may be fixator base elements that form a complete ring (full ring) or a segment or portion of a ring (e.g., half ring, ⅓ ring, ¼ ring, ⅜ ring, ⅝ ring, ⅔ ring, ¾ ring, and other) that is either used alone or joined with other segments or portions of the ring to form a fixator ring (not shown). The fixator rings 102a and 102b may be fixator base elements that are constructed of any material that provides the structural rigidity necessary for fixation such as metal, alloy, carbon fiber, plastic, ceramic and so forth. Moreover, the material comprising the rings 102a and 102b may be radiotranslucent.

The strut 106 is an active strut that is adjustable in six degrees of freedom. The strut 106 includes a first joint 122 and a second joint 124 connected by a center portion 126. The first joint 122 includes a first driven element 128 that connects to one of the strut mounting positions 104 of the first fixator ring 102a. The second joint 124 includes a second driven element 130 that connects to one of the strut mounting positions 104 of the second fixator ring 102a. As discussed in greater detail below, the driven elements 128 and 130 can each be articulated in two degrees of freedom. For example, depending on the embodiment, the driven element 128 can be angularly and/or rotationally repositioned relative to the center portion 126 of the strut 106 and/or the driven element 130 can be angularly and/or rotationally repositioned relative to the center portion 126 of the strut 106. The center portion 126 can also be lengthwise adjustable and/or translationally and/or rotationally adjustable relative to one or both of the first and second joints 122 and 124. Such embodiments can allow for multiple degrees of freedom in repositioning the first fixator ring 102a relative to the second fixator ring 102b.

Figure 2:
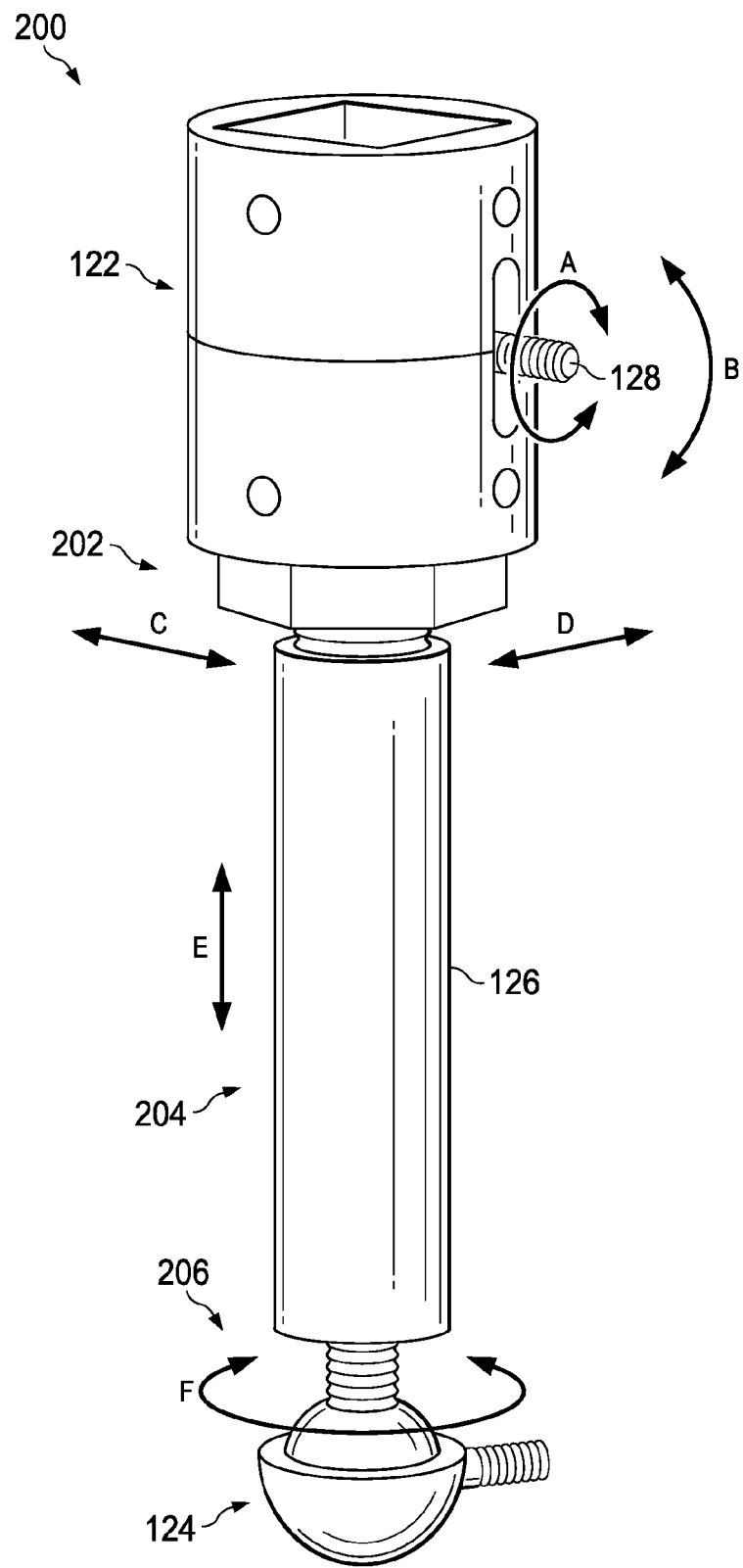
FIG. 2 is a perspective view of a fixator assembly according to one embodiment of the present disclosure.

FIG. 2 is a perspective view of a fixator assembly 200. The fixator assembly 200 can be used as the strut 106 of the fixator ring system 100, or can be used as a monolateral fixator. The fixator assembly 200 includes the first joint 122 and the second joint 124 as described above. The first and second joints 122 and 124 are connected by the center portion 126. The first joint 122 includes the driven element 128 that can be configured for connection to another fixator base element, such as the fixator ring 102a or 102b, or another type of fixator base element. As discussed in greater detail below, the driven element 128 can be angularly and/or rotationally repositioned relative to the center portion 126 of the fixator assembly 200, as illustrated by arrows A and B.

The fixator assembly 200 can include various other adjustable elements in order to allow for six degrees of freedom. For example, the fixator assembly 200 can include internal worm gears at adjustment position 202 for allowing adjustments to be made in directions indicated by arrows C and D; rack and pinion gears at adjustment position 204 for allowing adjustments to be made in directions indicated by arrow E; and rotational gearing at adjustment position 206 for allowing adjustments to be made in directions indicated by arrow F. The adjustable elements used to provide for adjustments in directions indicated by arrows C, D, E, and F can be selected from among a variety of know adjustment systems.

As described in greater detail below, a technician can lock the first joint 122 in a locked state where the driven element 128 is not free to move relative to other portions of the joint or fixator assembly 200. The technician can unlock the first joint 122 or otherwise place the first joint into an unlocked state for acute adjustments of the fixator assembly. In some embodiments, the first joint 122 can also be placed into a gradual-adjustment state for finer, more controlled movement and correction over time. The joint 122 can be manipulated either by hand or by a wrench on either one or multiple faces of the joint housing. Combining the two joint 122 with a strut body such as the center portion 126 and the second joint 124 can effectively allow for movement of two bone segments, fixator base elements, or other elements through six degrees of freedom.

The joint used as the first joint 122, and also as the second joint 124 in some embodiments, can be selected from the various embodiments of multiple-axis joints described in the present disclosure. Embodiments of the joint 122 can include a captured joint that can be driven in two degrees of freedom in order to achieve angulations and/or rotations about a single point in space. Embodiments can include a ball, which can be an at least partially spherically-shaped element, which may be hollow or solid, and which may have flat regions, projections, depressions, elements that extend therefrom and/or regions that are threaded, slotted, and/or otherwise provided with asperities. Embodiments of the joint 122 can include such a ball or nested ball/cylinder assembly that is securely captured in a housing such that a driven element can be oriented within a conical envelope protruding outward from the center of rotation. The ball or ball/cylinder assembly can be directly acted on by a driving mechanism (various exemplary forms detailed herein) that can be either automated or manually operated in order to achieve rotation and/or angulation of the ball itself. This joint can be used as part of an external fixator in order to move a fixator base element, bone segment, or other attachment through these degrees of freedom accurately.

Thus, the fixator assembly 200 constitutes an example of a single strut that can used in a monolateral configuration with attachments connected to each end thereof that could connect to a fixation element, such as a half-pin. First, fixation elements are inserted and attached to bone segments. Second, the fixator assembly 200 is unlocked and each end can include a driven element 128 that is attached to the appropriate fixation element and acute adjustment would be made, if necessary. Third, the fixator assembly 200 would be locked to hold the bone segments in place. Next, gradual adjustments could be made over time by unlocking the assembly 200, adjusting the driven elements 128, and then once again locking the assembly 200. This gradual adjustment over time could move two bone segments relative to each other in all six degrees of freedom.

Figure 3A:
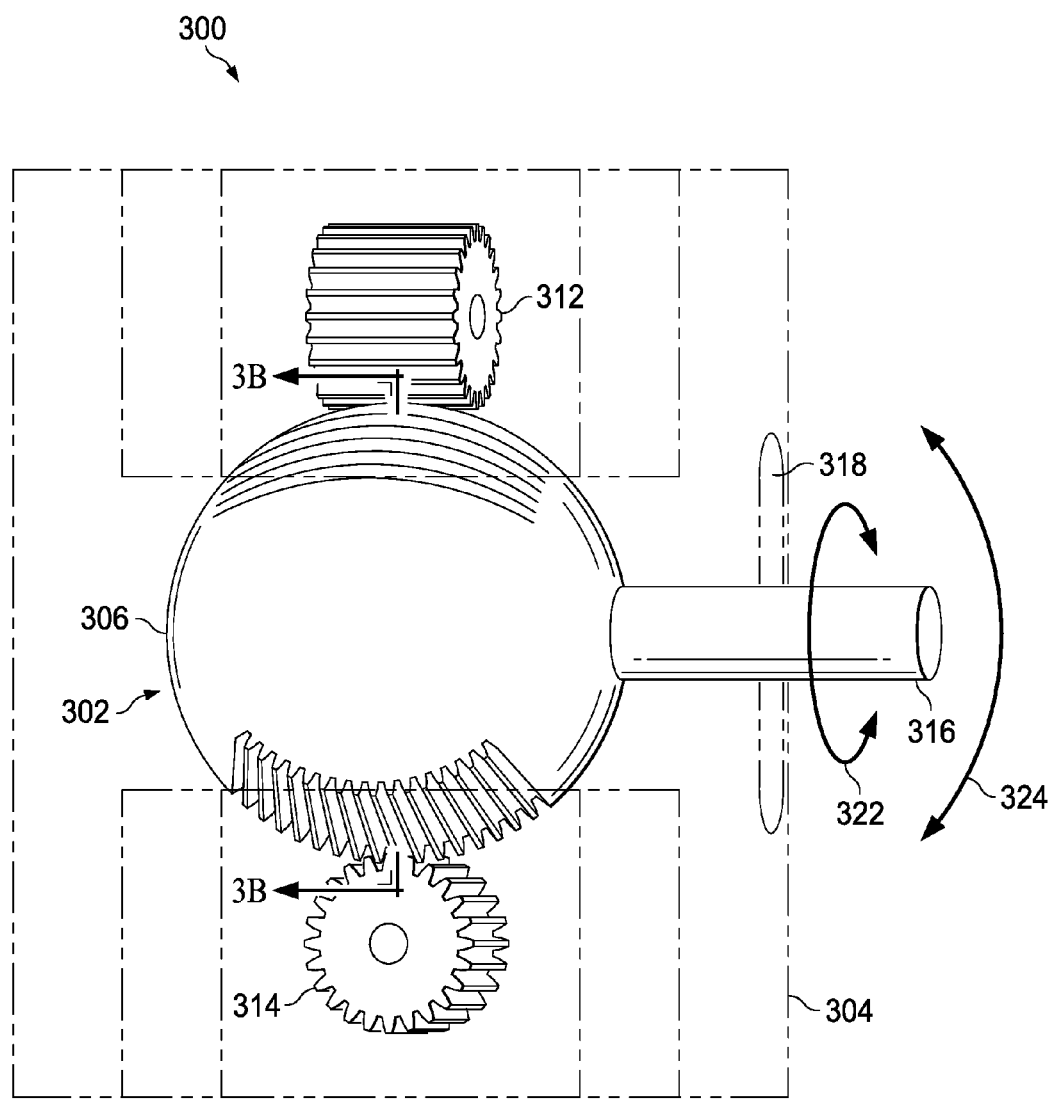
FIG. 3A is a perspective view of a first embodiment of a multiple-axis joint according to the present disclosure.
Figure 3B:
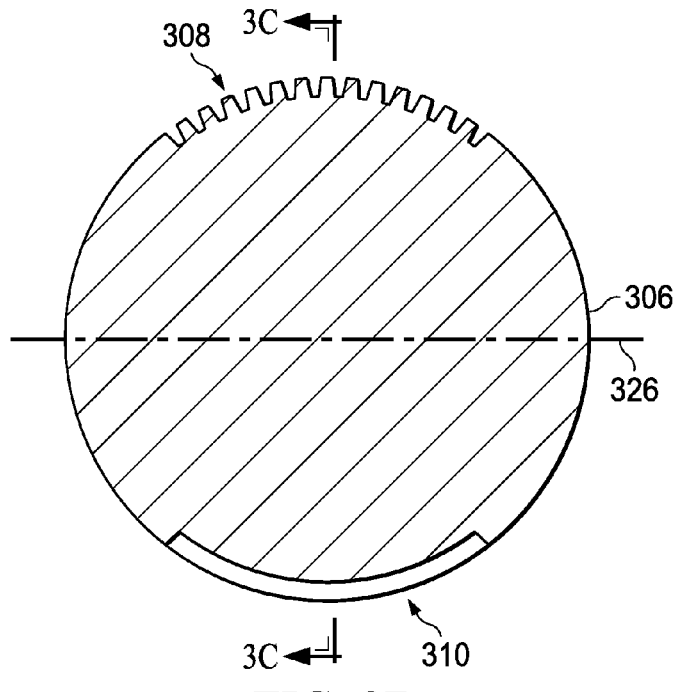
FIG. 3B is a cross-sectional view of a portion of the first embodiment of the multiple-axis joint taken along section lines 3B-3B shown in FIG. 3A.
Figure 3D:
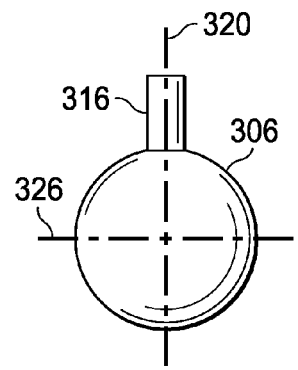
FIG. 3D is a top view of a portion of the first embodiment of the multiple-axis joint shown in FIG. 3B.
Figure 3C:
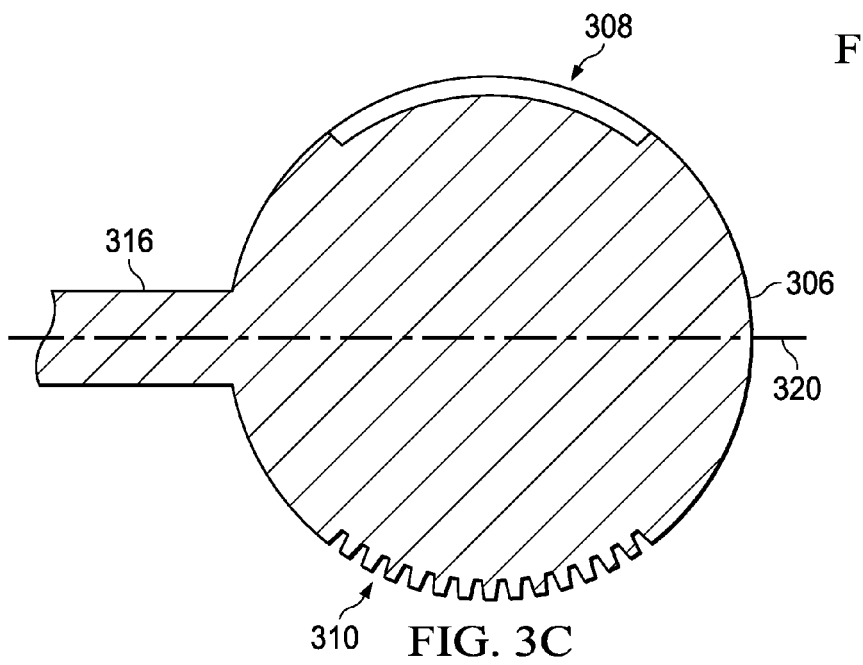
FIG. 3C is a cross-sectional view of a portion of the first embodiment of the multiple-axis joint taken along section lines 3C-3C shown in FIG. 3B.

FIGS. 3A through 3D show a first embodiment of a multiple-axis joint, generally designated as multiple-axis joint 300. FIG. 3A shows a perspective view of the joint 300. The joint 300 includes a ball joint 302 captured within a housing 304. The ball joint 302 includes a ball 306, which serves as an example of a spherically-shaped element. FIG. 3B shows a cross-sectional view of the ball 306 taken along section lines 3B-3B shown in FIG. 3A. FIG. 3C shows a cross-sectional view of the ball 306 taken along section lines 3C-3C shown in FIG. 3B. FIG. 3D shows a top view of the ball 306, illustrating the axes of rotation.

The ball 306 includes two sets of gear teeth 308 and 310. The gear teeth 308 and 310 are cut into the ball 306, for example in a radial or circumferential configuration, and extend in respective directions that are 90 degrees from one another. A first gear 312 is mated with the first set of gear teeth 308. A second gear 314 is mated with the second set of gear teeth 310. A driven element 316 is rigidly attached to the ball 306 and extends out of the housing 304 through a slot 318. Rotation of the first gear 312 will rotate the ball 306 within the housing 304. Rotation of the second gear 314 will angulate the ball 306 within the housing 304.

Depending on the embodiment, the first and second gears 312 and 314 can be rotated, directly or indirectly, by the technician in order to adjust the position of the driven element 316. In some embodiments, the gears 312 and 314 can be connected, directly or indirectly, to respective knobs, handles, or the like that can be used by the technician for adjusting the position of the driven element 316. In some embodiments, the gears 312 and 314 can be configured to be drivable, directly or indirectly, by a removable tool such as a hex key, screwdriver, or other tool that a technician can use in order to adjust the position of the driven element 316. For example, each of the gears 312 and 314 can include a slot or the like, and the housing 300 can include an access hole through which a tool can be inserted and mated with the gears 312 and 314 so that the technician can rotate the gears 312 and 314, and thereby adjust the position of the driven element 316. In some embodiments, each of the gears 312 and 314 can be attached to a respective drive shaft that extends from the gear 312, 314 and can be rotated either directly or using a removable tool such that rotation of the drive shafts adjusts the position of the driven element 316. Still further embodiments can include any desired configuration for allowing a technician to perform an action that causes rotation of selected gears 312 and 314 so that the technician can adjust the position of the driven element 316.

The first gear 312 can be rotated for driving the ball 306 such that the driven element 316 is rotationally articulated about a first axis of rotation 320 in directions indicated by arrows 322. As the first gear 312 is rotated, the ball 306 rotates and the gear teeth 310 slide within the gear teeth of the second gear 314, thereby allowing rotation of the driven element 316 independently of angulation of the driven element 316. The second gear 314 can be rotated for rotating the ball 306 about a second axis of rotation 326 such that the driven element 316 is angularly articulated, angulating the first axis of rotation 320, thereby moving the driven element in directions indicated by arrows 324. As the second gear 314 is rotated, the ball 306 rotates and the gear teeth 308 slide within the gear teeth of the first gear 312, thereby allowing angulation of the driven element 316 independently of rotation of the driven element 316. As shown in FIG. 3D, the first and second axes 320 and 326 extend through the center of the ball 306. The first axis of rotation 320 extends through the center of the ball 306 in a direction that is at least substantially perpendicular to the second axis of rotation 326. The first and second axes of rotation 320 and 326 intersect at a common rotation point about which the driven element 316 can be driven in two directions or degrees of freedom. The common rotation point is preferably at, or substantially near, the center of the ball 306, thus allowing the driven element 316 to be intuitively adjusted in two degrees of freedom that intersect at a common point of rotation that is at or substantially near the center of the ball 306. Note that the first set of gear teeth 308 on top of ball 306 are not shown in FIG. 3D so that the first and second axes of rotation 320 and 326 can be more clearly shown.

In some embodiments, the gears 312 and 314 can be repositioned relative to the ball 306 so as to be in contact with the ball 306 in a first position as shown in FIG. 3A, and to be out of contact with the ball 306 in a second position. For example, in some embodiments, the gears 312 and 314 can be slid or otherwise moved in and out of contact with the ball 306. When the gears 312 and 314 are in contact with the ball 306, the gears 312 and 314 act as a break to prevent movement of the ball 306 unless one or both of the gears 312 and 314 are rotating to drive the ball 306. Thus, when the gears 312 and 314 are in contact with the ball 306, the gears 312 and 314 act to effectively lock the joint 300. However, once the gears 312 and 314 are moved out of contact with the ball 306 such that the first gear 312 is no longer mated with the first set of gear teeth 308 and the second gear 314 is no longer mated with the second set of gear teeth 310, the ball 306 can freely move, thus allowing for acute adjustments of the position of the driven element 316.

Figure 4A:
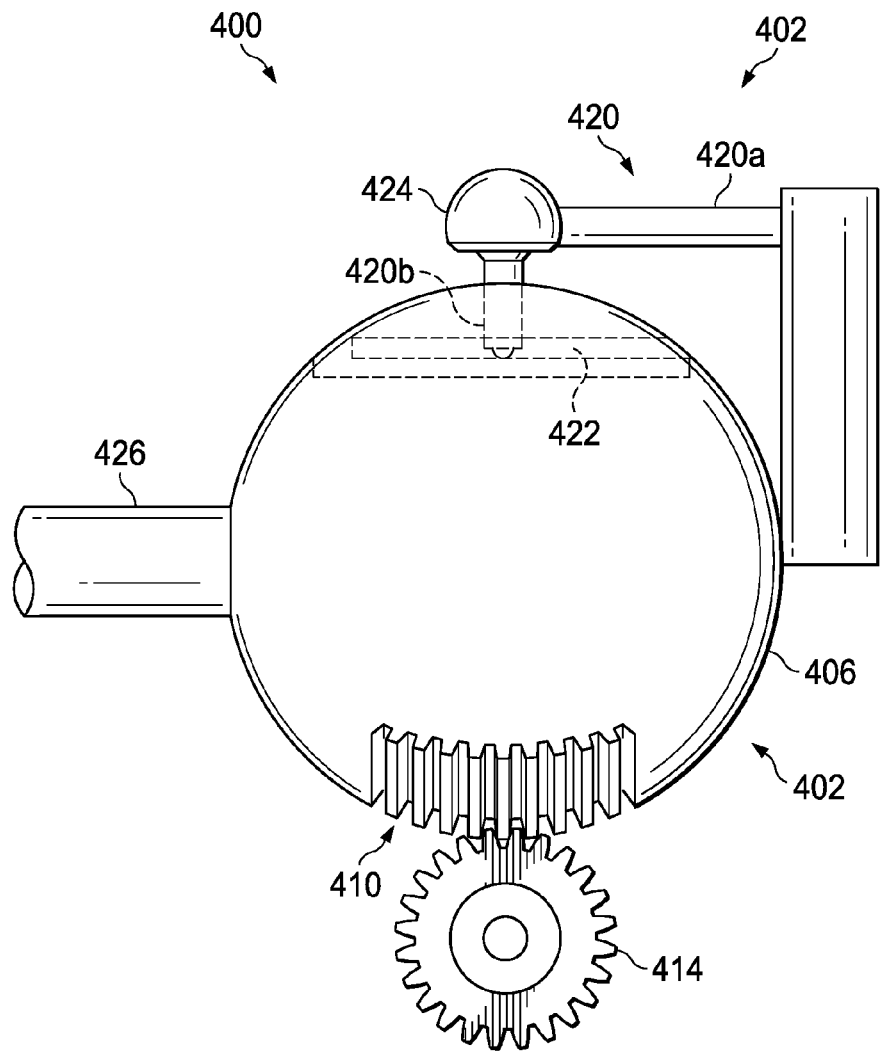
FIG. 4A is a perspective view of a second embodiment of a multiple-axis joint according to the present disclosure.
Figure 4B:
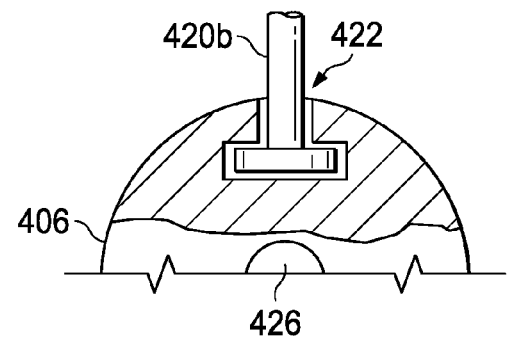
FIG. 4B is a partially-sectioned view of a portion of the joint shown in FIG. 4A.

FIGS. 4A and 4B show a second embodiment of a multiple-axis joint, generally designated as multiple-axis joint 400. FIG. 4A shows a perspective view of the joint 400. The joint 400 can be similar to joint 300, but includes a self-finding arm mechanism 402 in place of one of the gears and sets of gear teeth of joint 300. In alternative embodiments, the self-finding arm mechanism 402 can be in addition to the use the gears and sets of gear teeth of joint 300 discussed above.

The joint 400 can include a housing, such as housing 304; however, the housing is not shown in FIG. 4 for purposes of clarity. The joint 400 includes a ball joint 402. The ball joint 402 includes a ball 406, which serves as an example of a spherically-shaped element. The ball 406 includes a set of gear teeth 410. The gear teeth 410 are cut into the ball 406, for example in a radial or circumferential configuration. A gear 414 is mated with the set of gear teeth 410.

The joint 400 incorporates the usage of the gear 414 to angulate the ball 406 and the arm mechanism 402 to rotate the ball 406. The arm mechanism 402 includes an arm 420 that acts within a slot 422 in the top of the ball 406. FIG. 4B shows a partially-sectioned view illustrating a view of the arm 420 within the slot 422. Rotation of the arm 420 rotates the ball about the first axis of rotation 320 as shown in FIG. 3D, whereas the gear 414 rotates the ball about the second axis of rotation 326 as shown in FIG. 3D. The arm 420 includes a first arm section 420a and a second arm section 420b connected by a joint 424. The joint 424 can incorporate a universal joint, a ball and socket, or other mechanism to allow for the arm 420 to rotate the ball 406 about the first axis of rotation 320. A driven element 426 is rigidly attached to the ball 406 and extends out of the housing (not shown).

Thus, the ball 406 can include the same first and second axes of rotation 320 and 326 as shown in FIG. 3D in connection with ball 306. When the arm 420 is rotated, the gear teeth 410 in the bottom of the ball 406 can slide within the gear 414, allowing rotation of the ball 406 about the first axis of rotation 320 independently of angulation of the driven element 406. When the gear 414 is rotated, the joint 424 in the arm mechanism 402 can pivot as the ball 406 is rotated about the second axis of rotation 326, allowing angulation of the driven element 406 independently of rotation of the driven element 406.

In some embodiments, the gear 414 and arm mechanism 402 can be repositioned relative to the ball 406 so as to be in contact with the ball 406 in a first position as shown in FIG. 4, and to be out of contact with the ball 406 in a second position. For example, in some embodiments, the gear 414 and arm mechanism 402 can be moved in and out of contact with the ball 406. When the gear 414 and arm mechanism 402 are in contact with the ball 406, the gear 414 and arm mechanism 402 act as a break to prevent movement of the ball 406 unless one or both of the gear 414 and arm mechanism 402 are driving rotation of the ball 306. Thus, when the gear 414 and arm mechanism 402 are in contact with the ball 406, the gear 414 and arm mechanism 402 act to effectively lock the joint 400. However, once the gear 414 and arm mechanism 402 are moved out of contact with the ball 406 such that the arm mechanism 402 is no longer mated with the slot 422 and the gear 414 is no longer mated with the set of gear teeth 410, the ball 406 can freely move, thus allowing for acute adjustments of the position of the driven element 406.

Figure 5A:
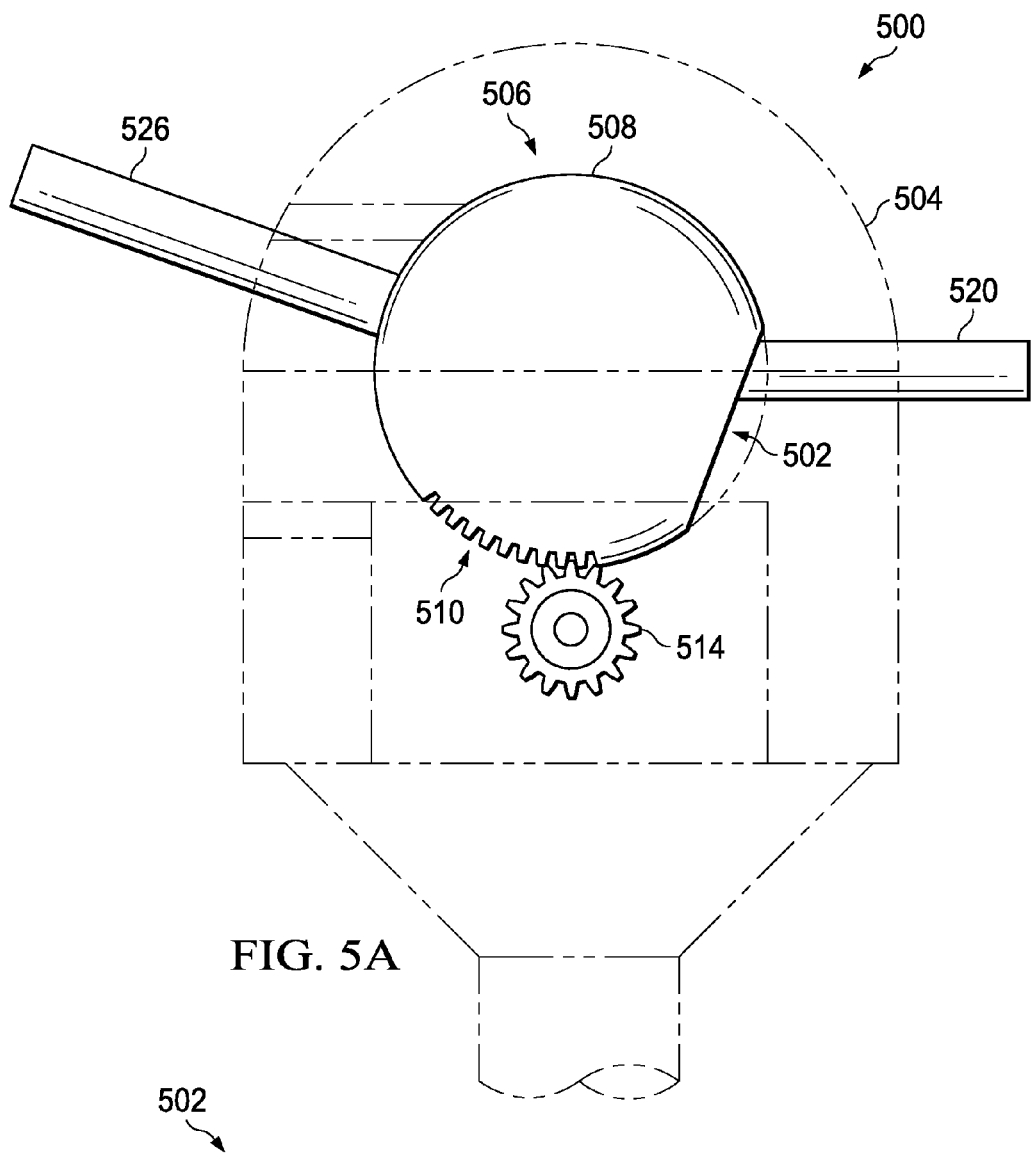
FIG. 5A is a perspective view of a third embodiment of a multiple-axis joint according to the present disclosure.
Figure 5C:
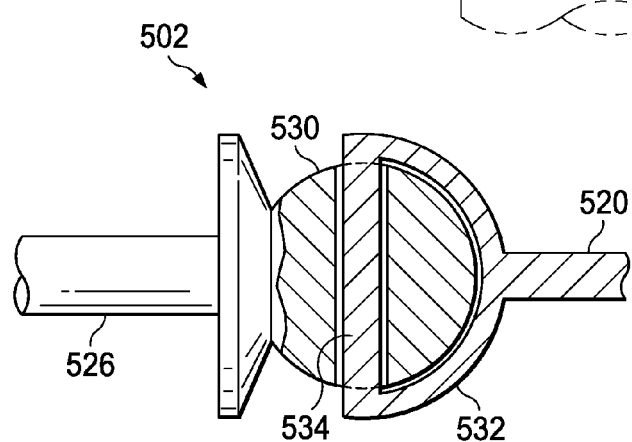
FIG. 5C is a partially-sectioned view of the internal joint shown in FIG. 5B.
Figure 5B:
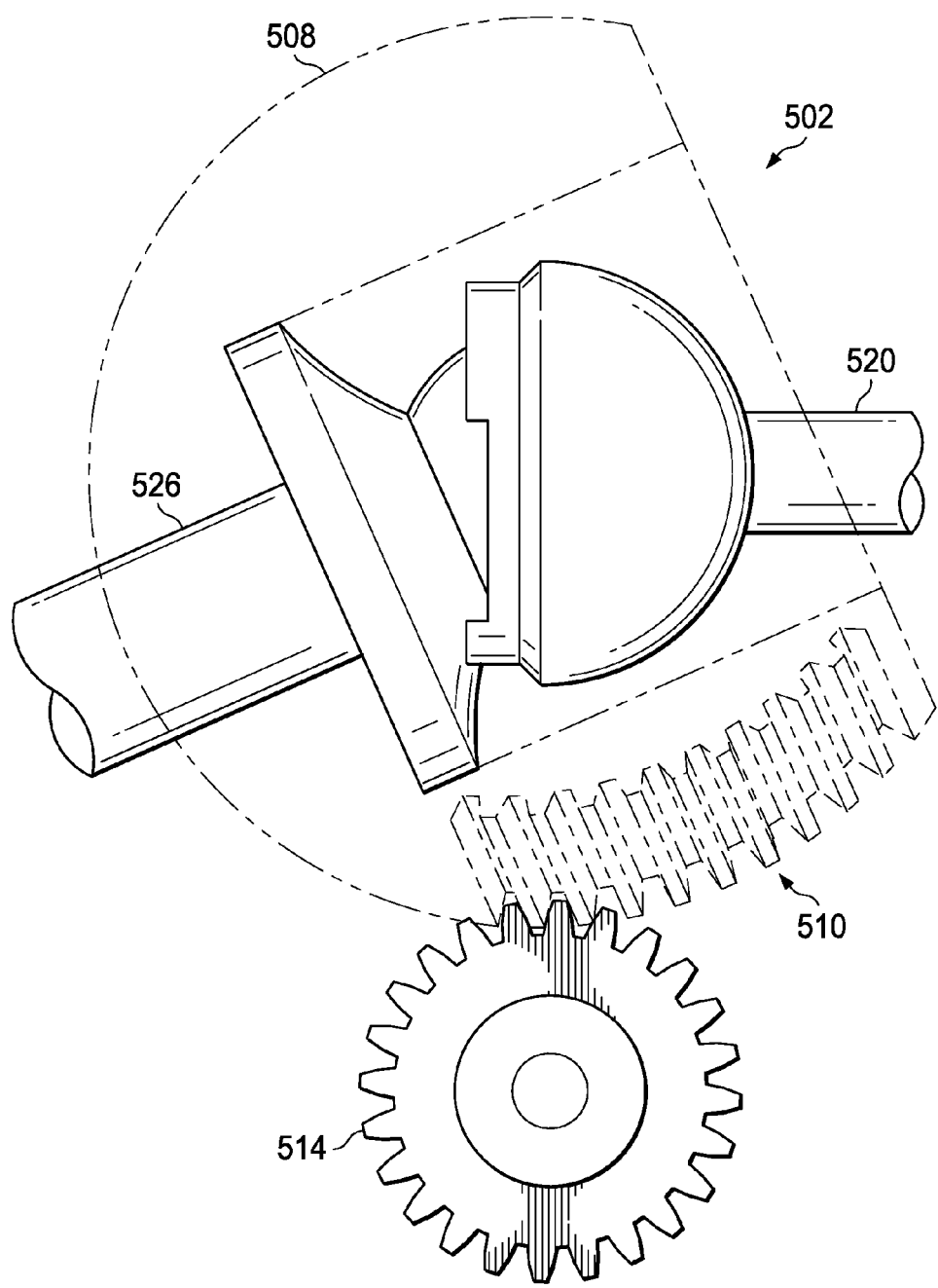
FIG. 5B is a view of an internal joint of the third embodiment of the multiple-axis joint shown in FIG. 5A.

FIGS. 5A through 5C show a third embodiment of a multiple-axis joint, generally designated as multiple-axis joint 500. FIG. 5A shows a perspective view of the joint 500. The joint 500 can be similar to joint 300, but incorporates an internal joint 502 placed at the center of a ball joint 506 to perform rotation in place of one of the gears and sets of gear teeth of joint 300. FIG. 5B shows a view of the internal joint 502, and FIG. 5C shows a partially-sectioned view of the internal joint 502.

The joint 500 includes a housing 504, and a ball joint 506 captured within the housing 504. The ball joint 506 includes a ball 508, which serves as an example of a spherically-shaped element. The ball 508 includes a set of gear teeth 510. The gear teeth 510 are cut into the ball 508, for example in a radial or circumferential configuration. A gear 514 is mated with the set of gear teeth 510. The joint 500 incorporates the use of the gear 514 to angulate the ball 508 and the internal joint 502 to rotate the ball 508.

The internal joint 502 can be controlled by a control arm 520 that connects to a universal joint, a ball and socket joint, a torque shaft/wire, or other mechanism suitable for rotating the driven element 526. For example, as shown in FIGS. 5B and 5C, the internal joint 502 can include an inner ball 530 and an outer ball 532, which serve as examples of spherically-shaped elements. Note that the ball 508 is not shown in FIG. 5C so that the internal joint 502 can be more clearly shown. The outer ball 532 is rigidly connected to the control arm 520, and the inner ball 530 is rigidly connected to the driven element 526. The outer ball 532 includes a pin 534 that extends through the inner ball 530. The pin 534 acts on the inner ball 532 such that the inner ball 532 rotates about the longitudinal axis of the driven element 526, corresponding to the first axis 320 shown in FIG. 3D, when the control arm 520 is rotated. In some embodiments, the inner ball 532 can be fixed relative to the ball 508 such that the ball 508 also rotates as the control arm 520, inner ball 530, and driven element 526 are rotated. In such embodiments, the driven element 526 can be attached to the ball 508 instead of to the inner ball 530 as shown in FIG. 5C, and the inner ball 530 can be fixed to the ball 508. In other embodiments, the inner ball 530 and driven element 526 can be free to rotate relative to the ball 508. In such embodiments, the driven element 526 can be fixed to the inner ball 530 as shown in FIG. 5C and pass through a hole through the ball 508.

The ball 506 can include the same first and second axes of rotation 320 and 326 as shown in FIG. 3D in connection with ball 306. When the control arm 520 is rotated, the gear teeth 510 in the bottom of the ball 506 can slide within the teeth of gear 514, allowing rotation of the ball 508 about the first axis of rotation 320 independently of angulation of the driven element 526. When the gear 514 is rotated, the gear 514 drives the ball 506 to rotate about the second axis of rotation 326, allowing angulation of the driven element 526 independently of rotation of the driven element 526. When the gear 514 is rotated, the internal joint 502 can pivot about pin 534, allowing angulation independently of rotation.

Figure 6A:
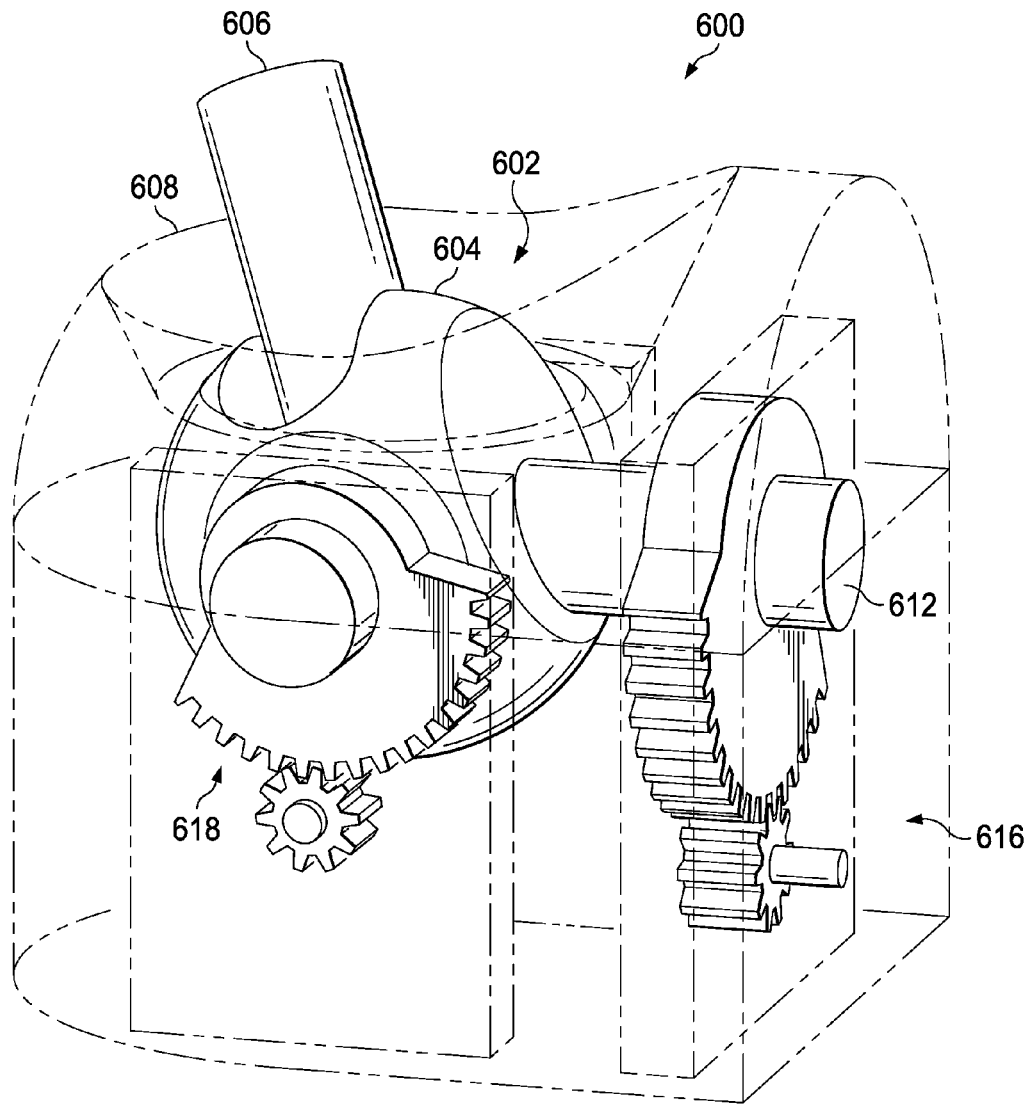
FIG. 6A is a perspective view of a fourth embodiment of a multiple-axis joint according to the present disclosure.
Figure 6B:
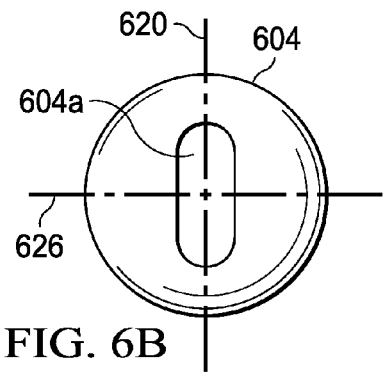
FIG. 6B is a top view of a portion of the joint shown in FIG. 6A.
Figure 7:
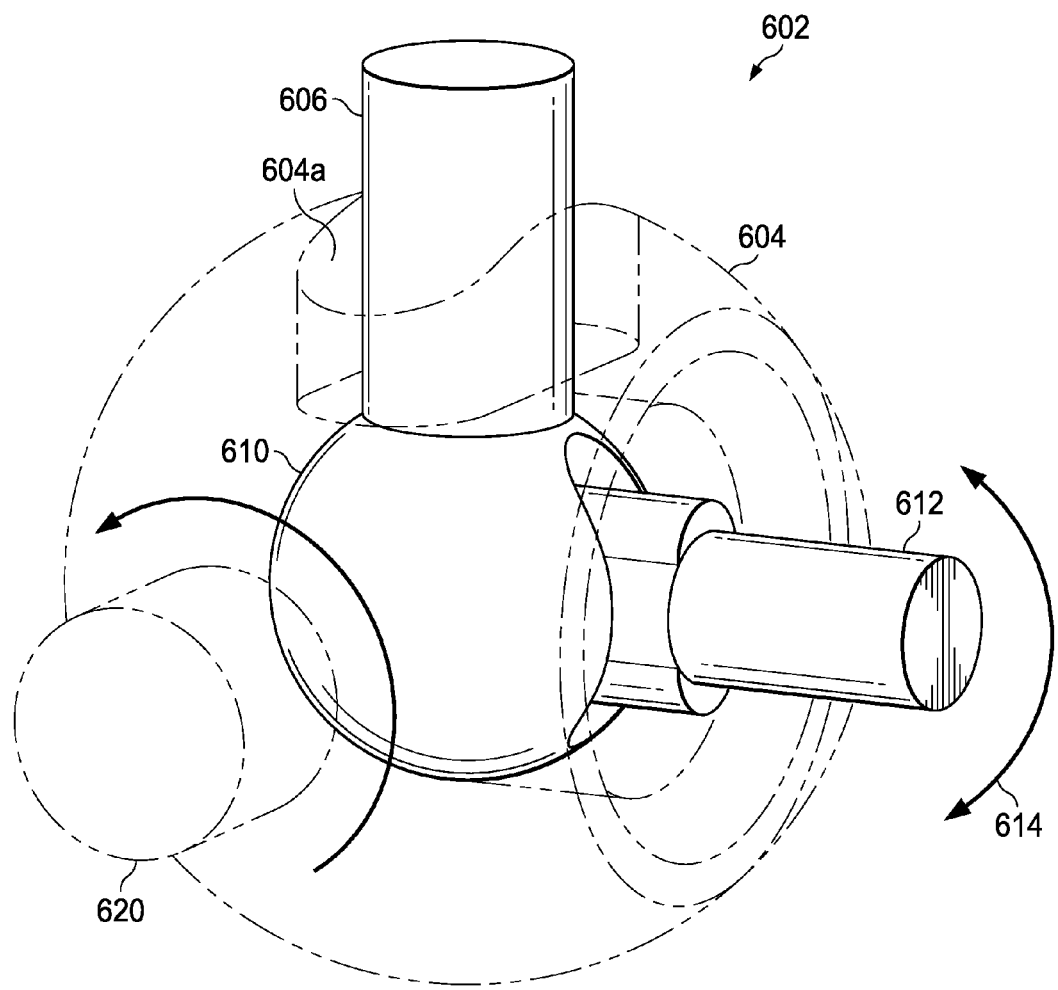
FIG. 7 is a view of an internal joint of the fourth embodiment of the multiple-axis joint shown in FIG. 6.

FIGS. 6A, 6B, and 7 show a fourth embodiment of a multiple-axis joint, generally designated as multiple-axis joint 600. FIG. 6A shows a perspective view of the joint 600. The joint 600 incorporates a ball joint 602 that includes an outer ball 604 and a driven element 606. Outer ball 604 serves as an example of a spherically-shaped element. FIG. 6B shows a top view of the outer ball 604, illustrating the axes of rotation 620 and 626 about which joint 600 can drive the driven element 606. The driven element 606 extends in a more generally vertical direction compared to the driven elements 316, 426, and 526 of the first through third embodiment joints 300, 400, and 500, respectively, which extend in a generally horizontal direction in a manner similar to the driven element 128 used with fixators 100 and 200 shown in FIGS. 1 and 2, respectively. This generally vertical orientation provides increased strength in tension and compression as compared to the more horizontal arrangement of the first through third embodiment joints 300, 400, and 500.

In the fourth embodiment, rotation of the ball joint 602 causes angulations of the driven element 606 in two degrees of freedom. Thus, unlike the first through third embodiments that include a first axis of rotation 320 that is coaxial with the driven element, the fourth embodiment joint 600 includes first and second axes of rotation 620 and 626 that are perpendicular to each other and to the longitudinal axis of the driven element 612. The first and second axes of rotation 620 and 626 intersect at a common rotation point about which the driven element 606 can be driven in two directions or degrees of freedom. The common rotation point is preferably at, or substantially near, the center of the outer ball 604, thus allowing the driven element 606 to be intuitively adjusted in two degrees of freedom that intersect at a common point of rotation that is preferably at or substantially near the center of the outer ball 604.

The ball joint 602 is captured within a housing 608. FIG. 7 shows the ball joint 602 without the housing 608 and other elements of the joint 600, and also shows portions of the ball joint 602 located within the outer ball 604. The ball joint 602 includes an inner ball 610 disposed concentrically within, and free to move relative to, the outer ball 604. The inner ball 610 serves as an example of a spherically-shaped element. The outer ball 604 can be driven to rotate in order to angulate the driven element 606 about the first rotational axis 620, while the inner ball 610 can be driven to rotate independently of the outer ball 604 for angulating the driven element 606 about the second rotational axis 626.

A first drive arm 612 is attached to the inner ball 610 such that the inner ball 610 rotates as the first drive arm 612 rotates about the longitudinal axis of the first drive arm 612, which corresponds to the second rotational axis 626. The driven element 606 is attached to the inner ball 610 and extends through the outer ball 604 through a slot 604a in the outer ball 604. The slot 604a defines a range of motion of the driven element 606 when driven by the first drive arm 612. The first drive arm 612 is pivotally attached to the inner ball 610, such that the first drive arm 612 is free to pivot relative to the inner ball 610 as indicated by arrow 614. As shown in FIG. 6, the first drive arm 612 can be driven by a first gear assembly 616. In alternative embodiments, the first gear assembly 616 can be replaced by a belt drive, a chain and sprocket drive, a torque shaft, a cable drive, or other such mechanisms.

A second drive arm 620 is rigidly attached to the outer ball 604 such that the outer ball 604 rotates as the second drive arm 620 rotates about the longitudinal axis of the second drive arm 612, which corresponds to the first rotational axis 620. The outer ball 604 can be driven by a second gear assembly 618. As shown in FIG. 6, the second drive arm 620 can be driven by a second gear assembly 616. In alternative embodiments, the second gear assembly 618 can be replaced by a belt drive, a chain and sprocket drive, a torque shaft, a cable drive, or other such mechanisms.

Figure 8:
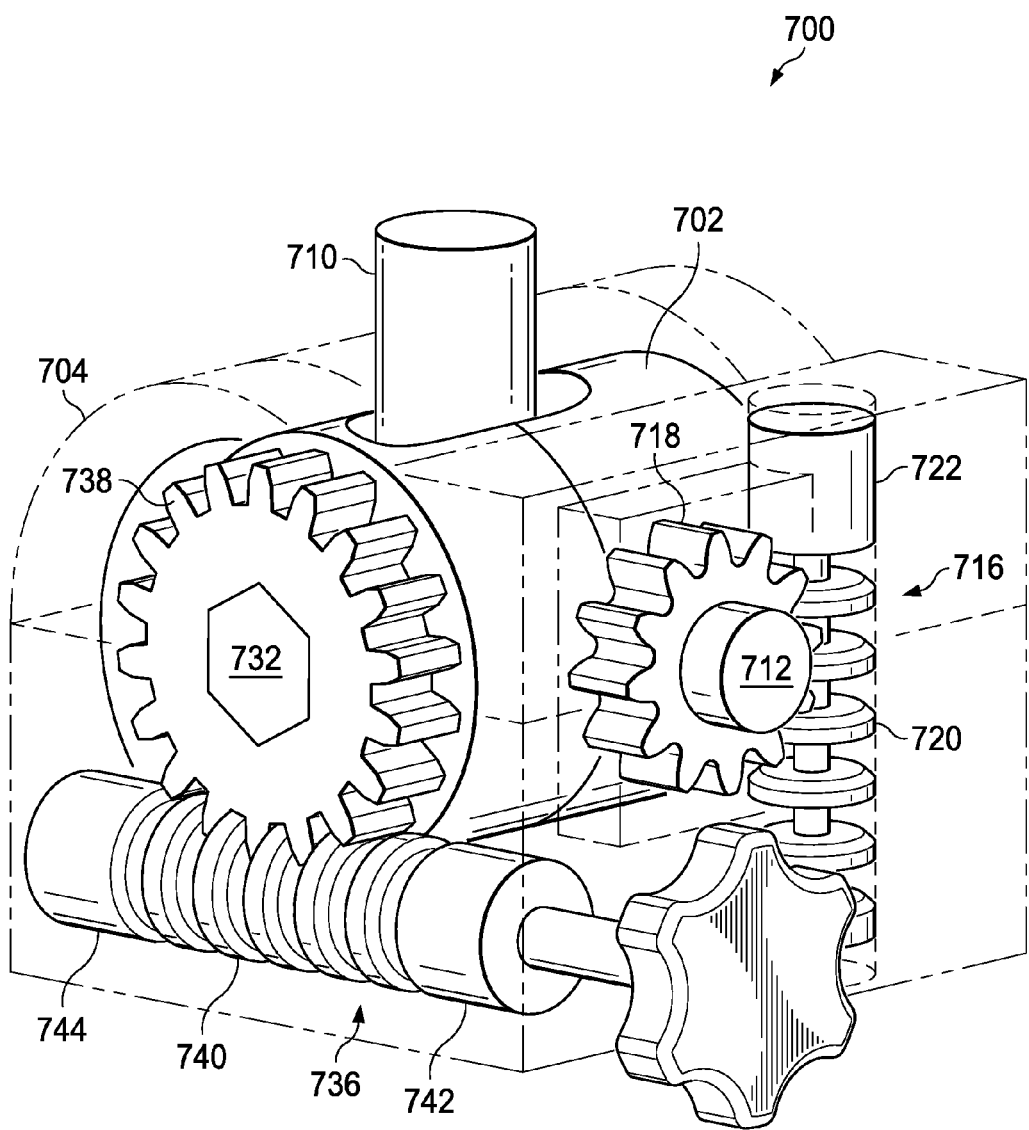
FIG. 8 is a perspective view of a fifth embodiment of a multiple-axis joint according to the present disclosure.
Figure 9:
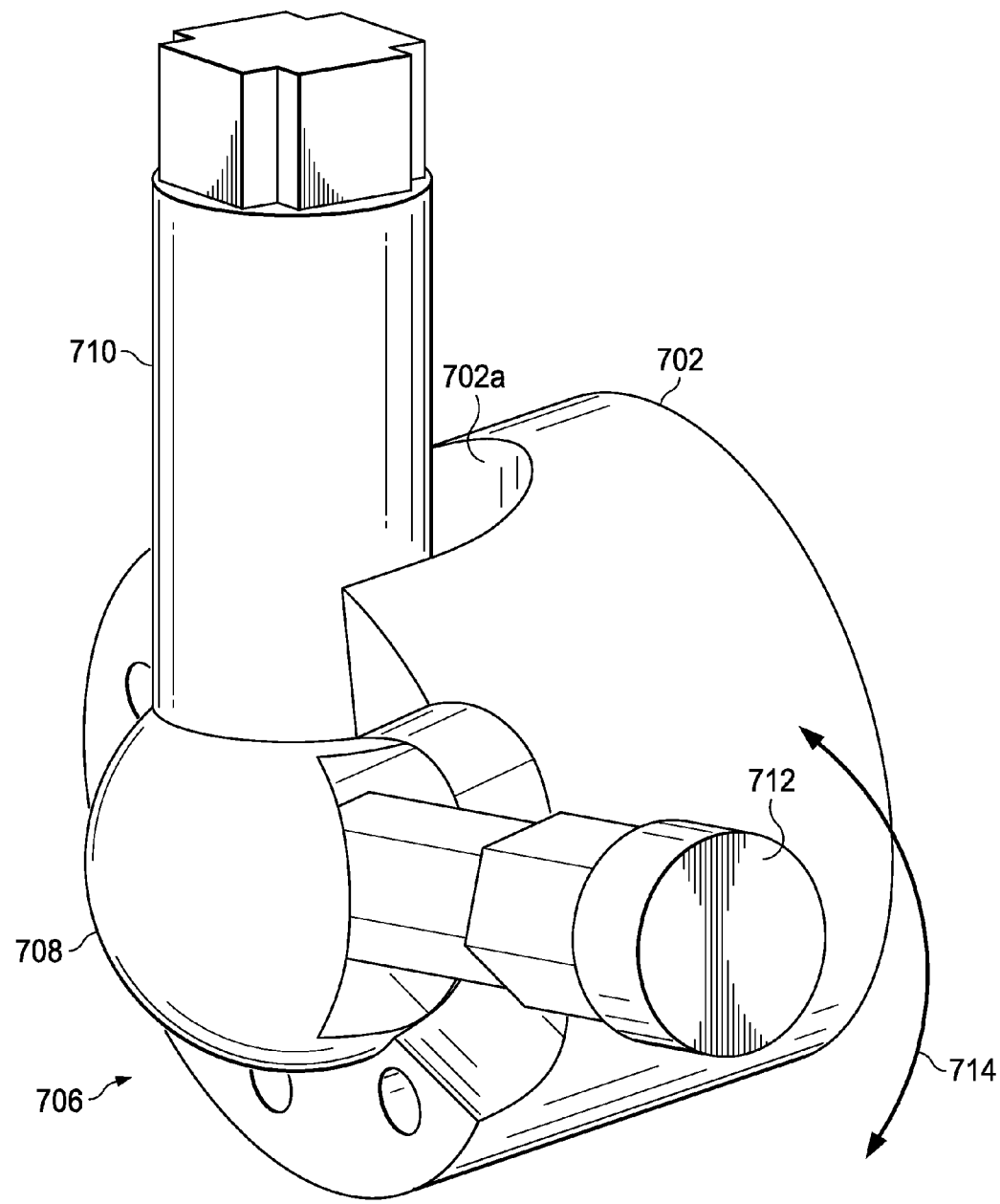
FIG. 9 is a view of an internal joint of the fifth embodiment of the multiple-axis joint shown in FIG. 8.

FIGS. 8 and 9 show a fifth embodiment of a multiple-axis joint, generally designated as multiple-axis joint 700. FIG. 8 shows a perspective view of the joint 700. The joint 700 includes a cylinder 702 captured within a housing 704. FIG. 9 shows a partially sectioned view of the cylinder 702, illustrating a ball joint 706 disposed within the cylinder 702.

The ball joint 706 includes a ball 708, which serves as an example of a spherically-shaped element, rigidly attached to a driven element 710. The joint 700 incorporates the ball joint 706 such that the driven element 710 extends in a generally vertical direction, similar to the fourth embodiment joint 600. The ball joint 706 also includes a first drive arm 712. The first drive arm 712 is attached to the ball 708 such that the ball 708 rotates as the first drive arm 712 rotates about the longitudinal axis of the first drive arm 712. The first drive arm 712 is pivotally attached to the ball 708, such that the first drive arm 712 is free to pivot relative to the ball 708 as indicated by arrow 714. The driven element 710 is attached to the ball 708 and extends through the cylinder 702 through a slot 702a in the cylinder 702. The slot 702a defines a range of motion of the driven element 710 when driven by the first drive arm 712.

The rotational axis of joint 700 are like those of the fourth embodiment joint 600 shown in FIG. 6B. Thus, the joint 700 includes first and second axes of rotation 620 and 626 that are perpendicular to each other and to the longitudinal axis of the driven element 710. The first and second axes of rotation 620 and 626 intersect at, or substantially near, the center of the cylinder 702, thus allowing the driven element 710 to be intuitively adjusted in two degrees of freedom that intersect at or substantially near the center of the cylinder 702. The ball 708 is disposed within, and free to move relative to, the cylinder 702. The cylinder 702 can be driven to rotate in order to angulate the driven element 710 about the first axis of rotation 620, while the ball 708 can be driven to rotate independently of the cylinder 702 for angulating the driven element 710 about the second axis of rotation 626.

The first drive arm 712 is rigidly attached to the ball 708 and can be driven by a first gear assembly 716. The first gear assembly 716 includes a first gear 718 that is rigidly attached to the first drive arm 712 such that the first drive arm 712 rotates with the first gear 718. The first gear assembly 716 also includes a first rack member 720. The first rack member 720 is a cylindrically cut rack having at least one threaded end 722. In addition, or alternatively, the first rack member 720 can have a second threaded end (not shown). The threaded end 722 mates with similar threads within the housing 704 such that rotation of the first rack member 720 about its longitudinal axis causes the first rack member 720 to move translationally along its longitudinal axis. The first rack member 720 can travel translationally and be rotated at the same time, allowing gear teeth of the first gear 718 to slide along the cylindrical cuts of the first rack member 720 as the first rack member 720 travels, thereby causing the first gear 718 to rotate. Rotation of the first gear 718 rotates the first drive arm 712, which in turn rotates the ball 708, which results in angulation of the driven element 710 about the second axis of rotation 626. In alternative embodiments, the first gear assembly 716 can be replaced by a belt drive, a chain and sprocket drive, a torque shaft, a cable drive, or other such mechanisms. When the first rack member 720 is not being rotated, the threaded end 722 acts as a braking/holding mechanism with the threads providing the braking force in the direction parallel to the longitudinal axis of the first rack member 720. Thus, when the first rack member 720 is not being rotated, the first rack member 720 acts to lock the first gear 718 so that the first gear 718 cannot rotate, thereby preventing the ball 708 from angulating the driven element 710. In alternative embodiments, the rack member 720 can be cut at an angle rather than cut cylindrically, for example the rack member 720 can be a worm or include a worm portion, and in such embodiments the gear 718 can be a worm gear.

A second drive arm 732 is rigidly attached to the cylinder 702 can be driven by a second gear assembly 736. The second gear assembly 736 includes a second gear 738 that is rigidly attached to the second drive arm 732 such that the second drive arm 732 rotates with the second gear 738. The second gear assembly 736 also includes a second rack member 740. The second rack member 740 is a cylindrically cut rack having at least one threaded end 742. In addition, or alternatively, the second rack member 740 can have a second threaded end 744. The threaded end 742 and/or 744 mates with similar threads within the housing 704 such that rotation of the second rack member 740 about its longitudinal axis causes the second rack member 740 to move translationally along its longitudinal axis. The second rack member 740 can travel translationally and be rotated at the same time, allowing gear teeth of the second gear 738 to slide along the cylindrical cuts of the second rack member 740 as the second rack member 740 travels, thereby causing the second gear 738 to rotate. Rotation of the second gear 738 rotates the second drive arm 732, which in turn rotates the cylinder 702, which results in angulation of the driven element 710 about the first axis of rotation 620. In alternative embodiments, the second gear assembly 736 can be replaced by a belt drive, a chain and sprocket drive, a torque shaft, a cable drive, or other such mechanisms. When the second rack member 740 is not being rotated, the threaded end 742 acts as a braking/holding mechanism with the threads providing the braking force in the direction parallel to the longitudinal axis of the second rack member 740. Thus, when the second rack member 740 is not being rotated, the second rack member 740 acts to lock the second gear 738 so that the second gear 738 cannot rotate, thereby preventing the cylinder 702 from angulating the driven element 710. In alternative embodiments, the rack member 740 can be cut at an angle rather than cut cylindrically, for example the rack member 740 can be a worm or include a worm portion, and in such embodiments the gear 738 can be a worm gear.

Figure 10A:
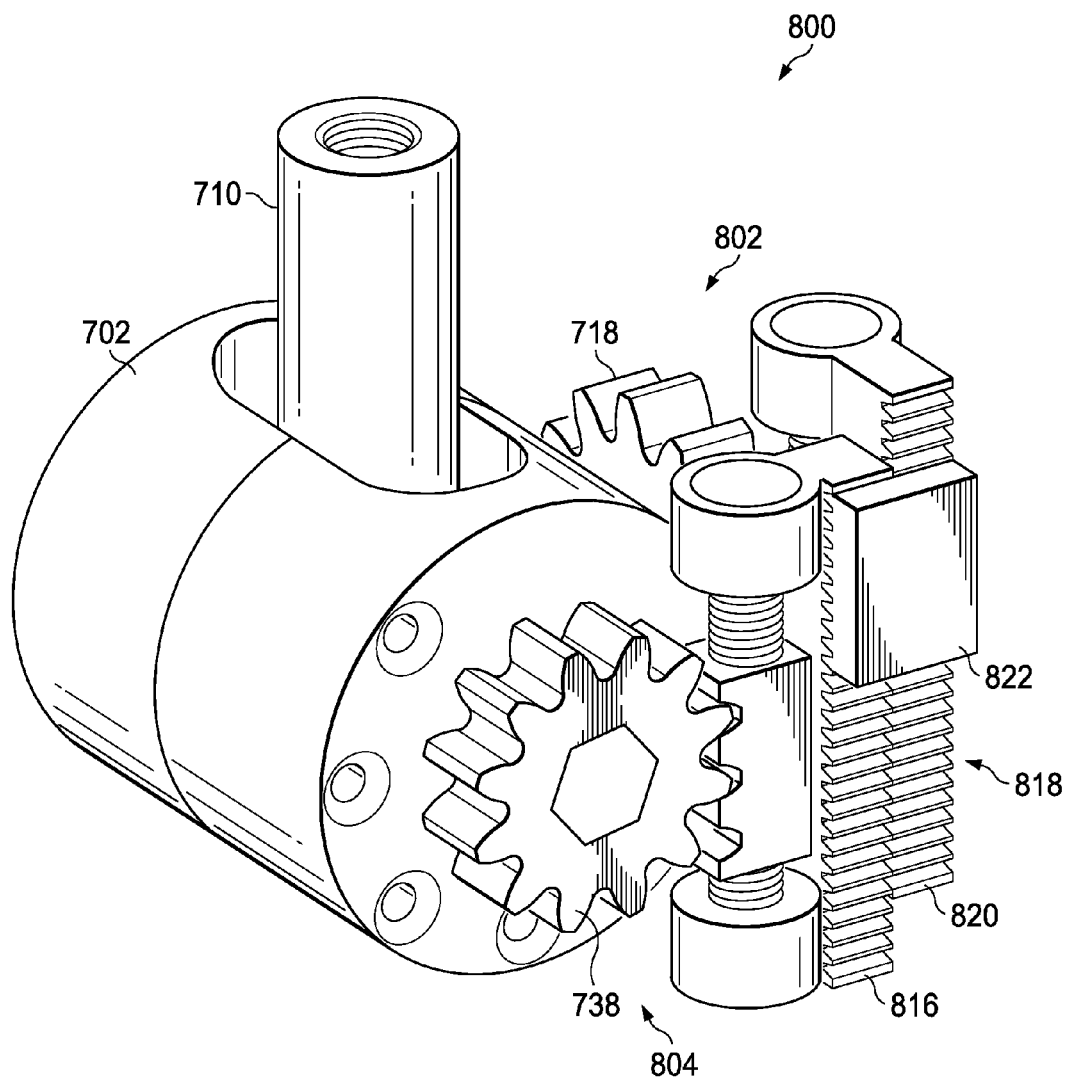
FIG. 10A is a perspective view of a sixth embodiment of a multiple-axis joint according to the present disclosure.
Figure 10B:
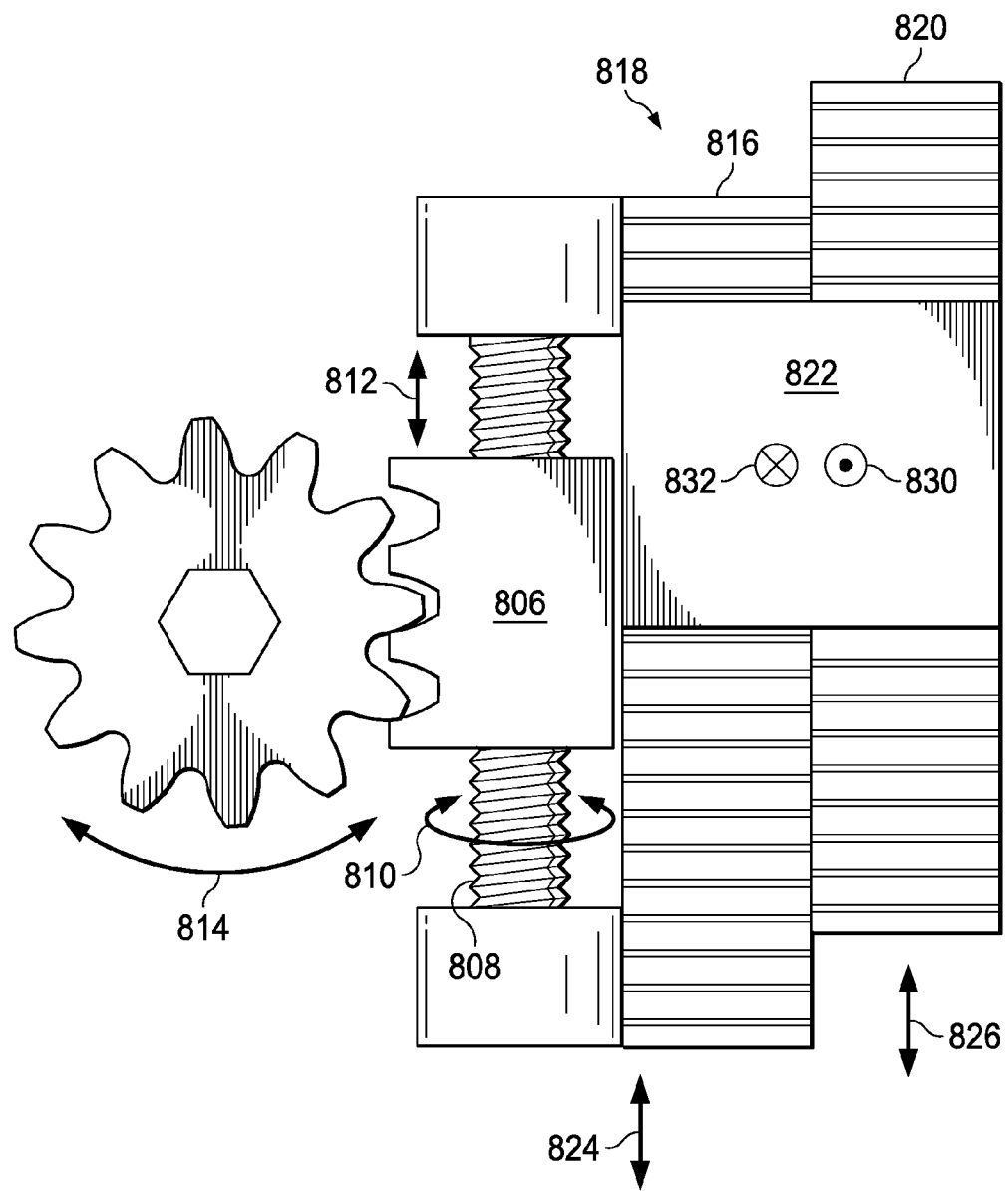
FIG. 10B is a view of a gear assembly and acute adjustment assembly of the sixth embodiment of the multiple-axis joint shown in FIG. 10A.

FIGS. 10A and 10B show a sixth embodiment of a multiple-axis joint, generally designated as multiple-axis joint 800. FIG. 10A shows a perspective view of the joint 800. The joint 800 can be substantially the same as joint 700, except for differences in the gear assemblies discussed below. The joint 800 includes a housing 704 as shown in FIG. 8. The joint 800 also includes a cylinder 702 and a ball joint 706 as shown in FIG. 9 and described in connection with joint 700. Elements of the joint 800 that can be the same or substantially the same as corresponding elements of joint 700 have retained the same element numbers, and the description of those like-numbered elements in connection with joint 700 applies equally to joint 800.

The joint 800 includes a first drive arm 712 rigidly attached to the ball 708 and a second drive arm 732 rigidly attached to the cylinder 702 as shown in FIGS. 8 and 9. A first gear assembly 802 includes a first gear 718 that is rigidly attached to the first drive arm 712. A second gear assembly 804 and a second gear 738 is rigidly attached to the second drive arm 732. The first and second gears 718 and 738 can angulate the driven element 710 as described above in connection with joint 700 about first and second rotational axes 620 and 626.

FIG. 10B shows an enlarged block diagram of the second gear assembly 804, as well as a portion of first gear assembly 802. The first and second gear assemblies 802 and 804 both allow for acute and finer or more gradual adjustments. The first and second gear assemblies 802 and 804 can be substantially the same; thus, the following description of the second gear assembly 804 applies equally to the first gear assembly 802.

The second gear assembly 804 includes a rack member 806 supported by a lead screw 808. The lead screw 808 can be rotated for fine/gradual adjustment of the driven element 710. Rotation of the lead screw 808 as indicated by arrow 810 causes the rack member 806 to translate along the lead screw 808 as indicated by arrow 812. The direction in which the rack member 806 travels relative to the rotation direction of the lead screw 808 will depend on the selected threading direction of the lead screw 808, which can vary for different embodiments. As the rack member 806 travels translationally along the lead screw 808, the rack member 806 engages with gear teeth of the second gear 738 causing the second gear 738 to rotate as indicated by arrow 814.

The second gear assembly 804 also includes a first acute adjustment block 816. The block 816 is part of an acute adjustment assembly 818 that also includes an acute adjustment block 820 of the first gear assembly 802. The acute adjustment assembly 818 includes a lock member 822. As shown in FIG. 10A, the adjustment blocks 816 and 820 include teeth that can mate with teeth of the lock member 822. As indicated in FIG. 10B, the lock member 822 can be pulled away from the adjustment blocks 816 and 820 in order to unlock the acute adjustment assembly 818. The lock member 822 can be pushed against the adjustment blocks 816 and 820 (position shown in FIG. 10A) in order to lock the acute adjustment assembly 818. Thus, the lock member 822 can be pulled away from the adjustment blocks 816 and 820 in order to unlock the acute adjustment assembly 818 and make acute adjustments to the driven element 710. While the lock member 822 is pulled away from the adjustment blocks 816 and 820, the adjustment blocks 816 and 820 can travel translationally, and independently of each other, in the directions indicated by arrows 824 and 826. The lead screw 808 is fixed relative to the adjustment block 816 such that the lead screw 808 translates with the adjustment block 816. The threads of the lead screw 808 carry the rack member 806 such that, if the lead screw is not rotating, the rack member 806 translates in directions 812 with the lead screw 808 and the adjustment block 816. As the rack member 806 travels translationally with the lead screw 808 and adjustment block 816, the rack member 806 engages with gear teeth of the second gear 738 causing the second gear 738 to rotate as indicated by arrow 814. This allows for a more acute adjustment of the driven element 710 about the first rotational axis 620 as compared to more gradual adjustments that can be made as described above by rotating the lead screw 810.

As mentioned above, the first gear assembly 802 can be identical or substantially the same as the second gear assembly 804. Thus, the driven element 710 can be acutely and gradually adjusted about the second rotational axis 626 via the first gear 718, first drive arm 712, and ball joint 706 using the first gear assembly 802 and acute adjustment assembly 818 in the same manner as describe above in connection with the second gear assembly 804.

The locking member 822 simultaneously engages and locks both of the adjustment blocks 816 and 820 when pushed in (direction into the page as indicated by direction 830 in FIG. 10B), and simultaneously disengages and unlocks both of the adjustment blocks 816 and 820 when pulled out (direction into the page as indicated by direction 832 in FIG. 10B). Thus, when the locking member 822 is moved to the unlocking position, the driven element 710 can be acutely adjusted along both the first and second rotational axes 620 and 626. In alternative embodiments, separate locking members 822 can be provided for each of the adjustment blocks 816 and 820. Such an embodiment allows for acute adjustment of only one of the rotational axes 620 and 626 at a time by unlocking only a selected one of the two locking members 822, or simultaneous acute adjustments by unlocking both of the locking members 822.

Figure 11:
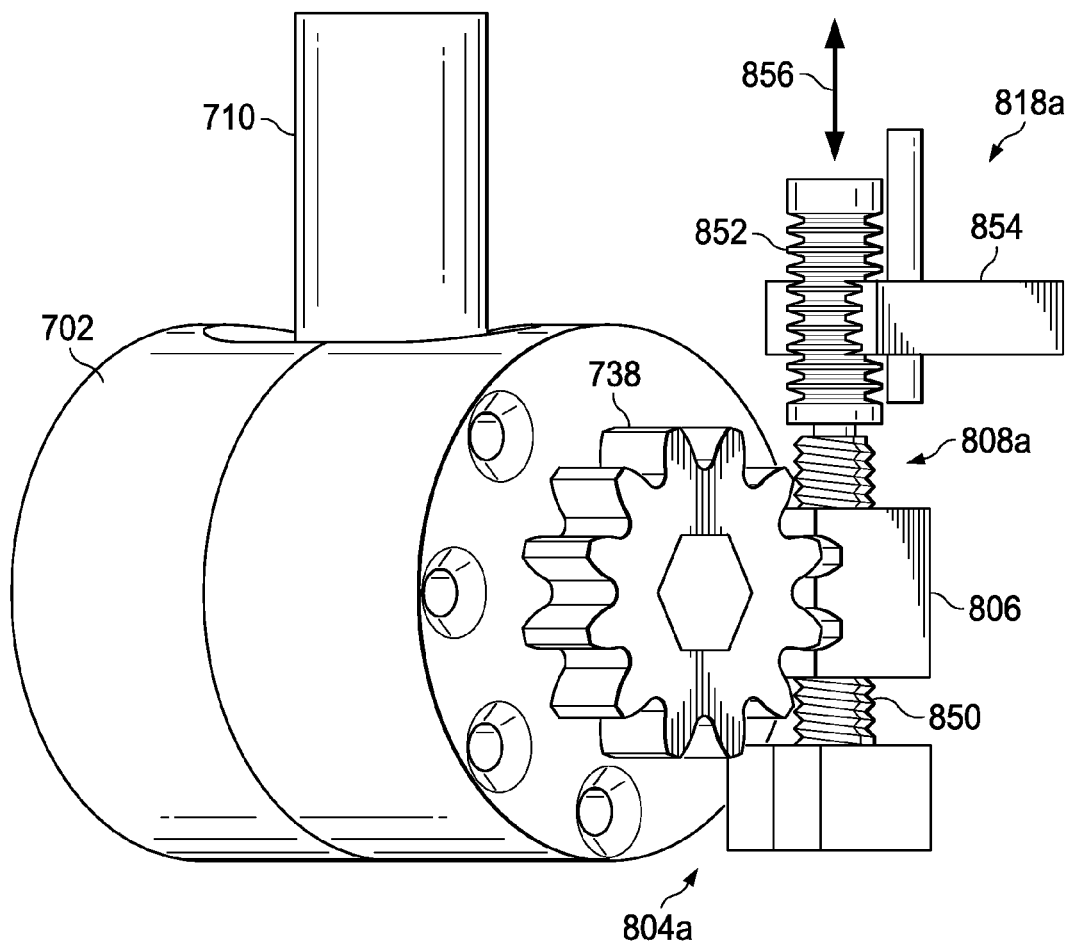
FIG. 11 is a view of an alternative gear assembly and acute adjustment assembly of the sixth embodiment of the multiple-axis joint shown in FIGS. 10A and 10B.

FIG. 11 shows an alternative second gear assembly 804a that can be used with the joint 800. The first gear assembly 802 can be similarly modified. The gear assembly 804a also allows for acute and finer or more gradual adjustments.

The second gear assembly 804a includes the rack member 806 supported by an alternative lead screw 808a. The lead screw 808a includes a helically threaded portion 850 that supports the rack member 806. The lead screw 808a also includes a cylindrically cut portion 852. The lead screw 808a can be rotated for fine/gradual adjustment of the driven element 710. Rotation of the lead screw 808a as indicated by arrow 810 in FIG. 10B causes the rack member 806 to translate along the lead screw 808a as indicated by arrow 812 in FIG. 10B. The direction in which the rack member 806 travels relative to the rotation direction of the lead screw 808a will depend on the selected threading direction of the threaded portion 850 of the lead screw 808a, which can vary for different embodiments. As the rack member 806 travels translationally along the lead screw 808a, the rack member 806 engages with gear teeth of the second gear 738 causing the second gear 738 to rotate as indicated by arrow 814 in FIG. 10B.

The second gear assembly 804a also includes an alternative acute adjustment assembly 818a that includes a lock member 854 and the cylindrically cut portion 852 of the lead screw 808a. The lock member 854 can be controlled to engage or disengage the cylindrical cuts of the cylindrically cut portion 852 of the lead screw 808a. The lock member 854 includes teeth that can mate with the cylindrical cuts of the cylindrically cut portion 852 of the lead screw 808a. The lock member 854 can be pulled away from the cylindrically cut portion 852 of the lead screw 808a in order to unlock the acute adjustment assembly 818a and thereby allow for acute adjustments of the second gear assembly 804a. The lock member 854 can be moved to engage the cylindrically cut portion 852 of the lead screw 808a (position shown in FIG. 11) in order to lock the acute adjustment assembly 818a. Thus, the lock member 854 can be pulled away from the cylindrically cut portion 852 of the lead screw 808a in order to unlock the acute adjustment assembly 818a and make acute adjustments to the driven element 710. While the lock member 854 is pulled away from the cylindrically cut portion 852 of the lead screw 808a, the lead screw 808a can travel translationally in the directions indicated by arrow 856. The threaded portion 850 of the lead screw 808a carry the rack member 806 such that, if the lead screw 808a is not rotating, the rack member 806 translates in directions 856 with the lead screw 808a. As the rack member 806 travels translationally with the lead screw 808a, the rack member 806 engages with gear teeth of the second gear 738 causing the second gear 738 to rotate as indicated by arrow 814 in FIG. 10B. This allows for a more acute adjustment of the driven element 710 about the first rotational axis 620 as compared to more gradual adjustments that can be made as described above by rotating the lead screw 810.

As mentioned above, an alternative first gear assembly 802 can be identical or substantially the same as the alternative second gear assembly 804a. Thus, the driven element 710 can be acutely and gradually adjusted about the second rotational axis 626 via the first gear 718, first drive arm 712, and ball joint 706 using the first gear assembly 802 and acute adjustment assembly 818a in the same manner as describe above in connection with the second gear assembly 804a.

Still further embodiments of multiple-axis joints include embodiments that combine various elements of the first through sixth embodiment joints 300, 400, 500, 600, 700, and 800. For example, the joints 300, 400, and 500 can be modified to include one or more gear assemblies, such as gear assemblies 616, 618, 716, 736, 802, and 804, and/or acute adjustment assemblies, such as acute adjustment assembly 818. More specifically, any of the gear assemblies 616, 618, 716, 736, 802, and 804 can be used to drive any of the gears 312, 314, 414, and 514. The gear assemblies 616, 618, 716, 736, 802, and 804 constitute examples of drive systems that can be driven manually, by way of a handle, knob, removable tool, key, or any other implement suitable for allowing a person to make manual adjustments for driving the driven element (such as driven element 316, 426, 526, 606, or 710) in a desired direction.

Any of the multiple-axis joints 300, 400, 500, 600, 700, and 800 and variations thereof can be used as the first joint 122 and/or the second joint 124 of the fixator ring system 100 or the fixator assembly 200. Still further embodiments of fixator ring systems that can include any of the multiple-axis joints described herein are described below in connection with FIGS. 12-14.

Figure 12:
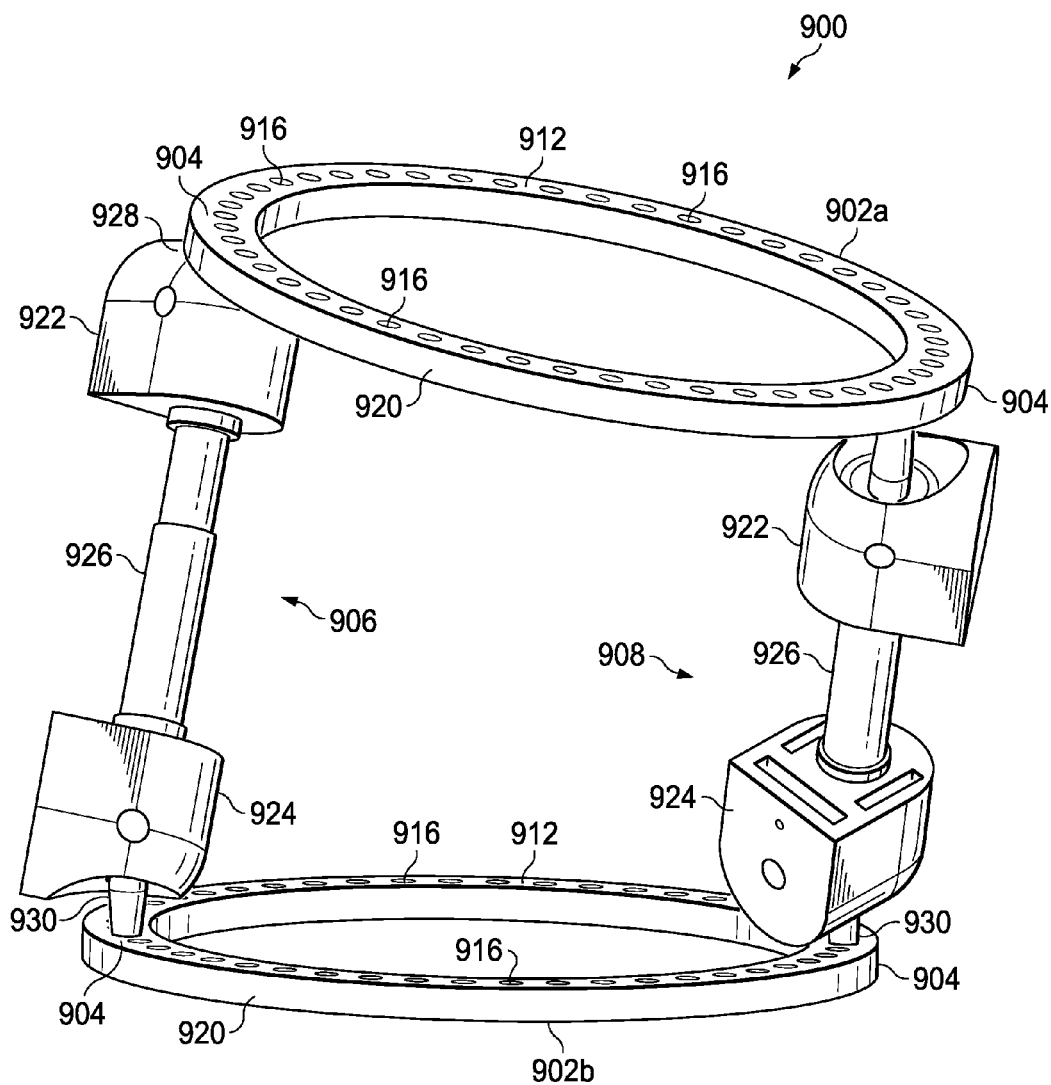
FIG. 12 is a perspective view of a first alternative embodiment of an external fixator ring system according to the present disclosure that includes a plurality of active struts.

FIG. 12 shows a perspective view of a first alternative embodiment of an external fixator ring system, generally designated as external fixator ring system 900. The fixator ring system 900 includes a first fixator ring 902a and a second fixator ring 902b, which serve as examples of fixator base elements. The fixator rings 902a and 902b both include a plurality of strut mounting positions 904. The fixator rings 902a and 902b are connected by a pair of connection struts 906 and 908. In this embodiment, both of the struts 906 and 908 are active struts. While two active struts 906 and 908 are shown, alternative embodiments can include more or fewer active struts.

The first fixator ring 902a includes a top surface 912 and an opposing bottom surface (not shown). The top surface 912 includes numerous holes 916 that extend through the top surface 912 to the bottom surface (not shown). The holes 916 may be used for attachment of wire and half pin fixation elements (bolts), threaded or telescopic connection rods, plates, posts or other device connection elements to the first fixator ring 902a. The outer side surface 920 of the first fixator ring 902a can include numerous threaded apertures (not shown) that provide additional attachment points for struts or other connection elements (not shown). The second fixator ring 902b can be identical or similar to the first fixator ring 902a.

Although the shape of the fixator rings 902a and 902b as shown FIG. 12 is substantially circular, the shape of the fixator rings 902a and 902b can vary to accommodate the physical contour of various body parts to which the fixation system 900 would be attached. For example, the fixator rings 902a and 902b can be fixator base elements configured to have an oval shape, D-shape, U-shape, C-shape, a polygon, or other irregular shapes. In some exemplary embodiments, an elliptical fixator ring (not shown) may be particularly advantageous. The insertion of pins or wires into a patient's limb can cause the surrounding tissue to swell unevenly, and in such a case, an elliptical fixator ring can accommodate the uneven swelling better than a circular ring can. The fixator rings 902a and 902b may be fixator base elements that form a complete ring (full ring) or a segment or portion of a ring (e.g., half ring, ⅓ ring, ¼ ring, ⅜ ring, ⅝ ring, ⅔ ring, ¾ ring, and other) that is either used alone or joined with other segments or portions of the ring to form a fixator ring (not shown). The fixator rings 902a and 902b may be fixator base elements constructed of any material that provides the structural rigidity necessary for fixation such as metal, alloy, carbon fiber, plastic, ceramic and so forth.

The strut 906 includes a first joint 922 and a second joint 924 connected by a center portion 926. The first joint 922 and second joint 924 are embodiments of multiple axis joints, such as the fourth, fifth, or sixth embodiment joints 600, 700, and 800, that include a generally vertical driven element. The first joint 922 includes a first driven element 928 that connects to one of the strut mounting positions 904 of the first fixator ring 902a. As discussed herein, the driven element 928 can be angularly and/or rotationally repositioned relative to the center portion 926 of the strut 906. The second joint 924 includes a second driven element 930 that connects to one of the strut mounting positions 904 of the second fixator ring 902b. As discussed herein, the driven element 930 can be angularly and/or rotationally repositioned relative to the center portion 926 of the strut 906. The connection strut 908 also includes first and second joints 922 and 924 and can be identical to the first connection strut 906.

The joints 922 and 924 of the struts 906 and 908 can be manipulated, for example by hand or using a tool such as a wrench, to angulate and/or rotate (depending on the joint) the driven elements 928 and 930. For example, the joints 922 and 924 can include set screws or the like on the housings thereof for allowing insertion of a wrench, screwdriver, or other such tool so that the user can drive the gears/gear assemblies (such as gears 312, 314, 414, and 514 and/or gear assemblies 616, 618, 716, 736, 802, and 804) and thereby reposition the driven elements 928 and 930.

The center portion 926 can be a strut body such as center portion 126 of the fixator assembly 200 shown in FIG. 2, which includes various adjustable elements in order to allow for six degrees of freedom. Combining two of the multiple-axis joints described herein with such a strut body can allow for effectively moving two bone segments, fixator base elements, or other elements through all six degrees of freedom.

Two struts such as struts 906 and 908 can thus be used with rings 902a and 902b in order to move two bone segments relative to one another. First, the rings 902a would be attached to bone segments with fixation elements such as half pins or k-wires. Second, the struts 906 and 908 would be unlocked and attached to the rings 902a and 902b with an angular separation preferably of greater than 90 degrees and an acute adjustment would be made, if necessary. Third, the struts 906 and 908 would be locked into an active-locked state so as to hold the bone segments in place. Next, gradual adjustment could be made over time by adjusting the driven elements 928 and 930 of the struts 906 and 908 while the struts 906 and 908 are in active-locked states. This gradual adjustment over time could move two bone segments relative to each other in all six degrees of freedom.

Figure 13:
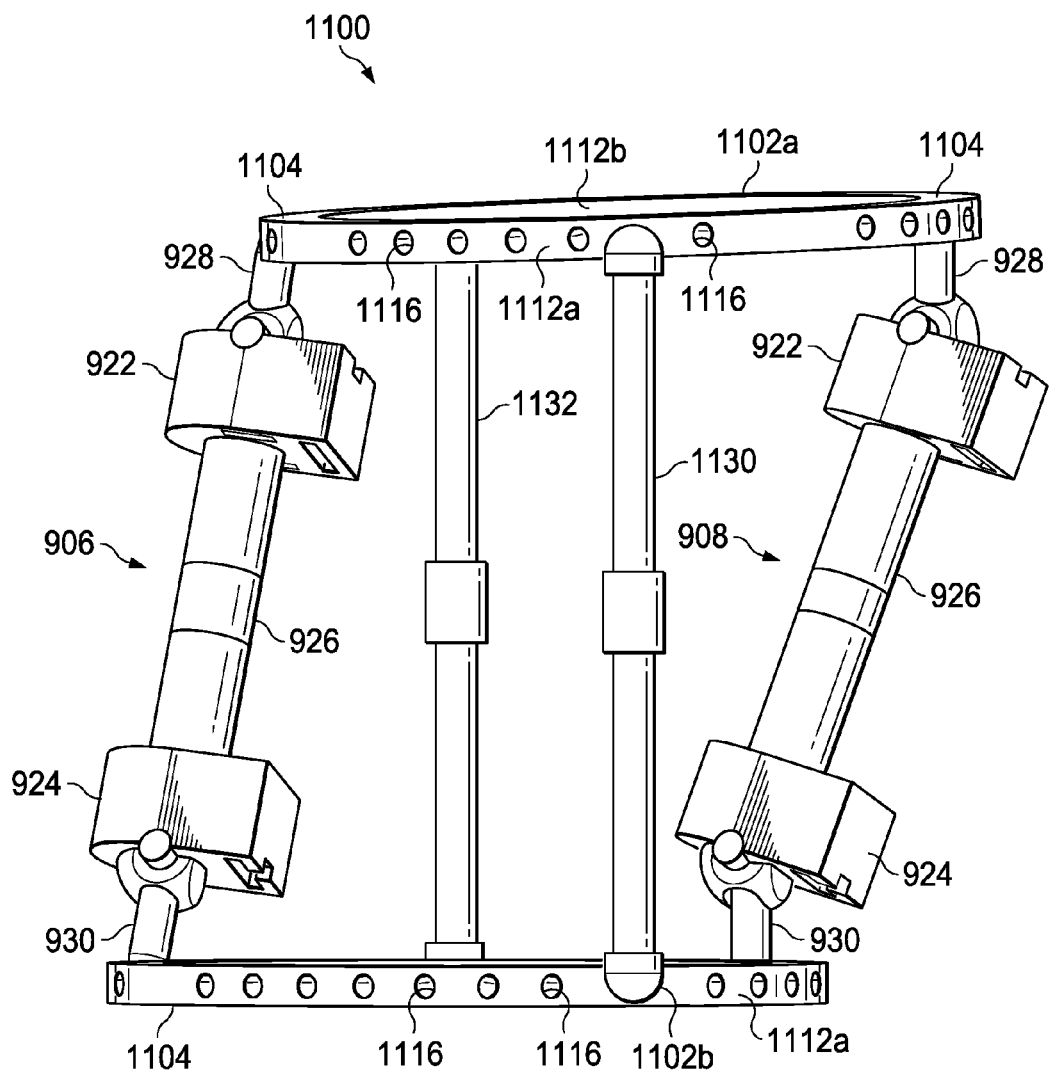
FIG. 13 is a perspective view of a second alternative embodiment of an external fixator ring system according to the present disclosure that includes a plurality of active struts in combination with a plurality of passive struts.

FIG. 13 shows a perspective view of a second alternative embodiment of an external fixator ring system, generally designated as external fixator ring system 1100. The fixator ring system 1100 includes a first fixator ring 1102a and a second fixator ring 1102b, which serve as examples of fixator base elements. The fixator rings 1102a and 1102b both include a plurality of strut mounting positions 1104. The fixator rings 1102a and 1102b are connected by a pair of active struts 906 and 908, which can be identical to the active struts 906 and 908 described above, wherein like elements of active struts 906 and 908 have retained like element numbers. The fixator rings 1102a and 1102b are also connected by a pair of passive struts 1130 and 1132, which can be the same as, or similar to, passive struts 108 and 110.

The first fixator ring 1102a includes an outer side surface 1112a and an opposing inner side surface 1112b. Numerous holes 1116 that extend through the outer side surface 1112a to the inner side surface 1112b. The holes 1116 may be used for attachment of threaded or telescopic connection rods 1130 and 1132 between the first and second fixator rings 1102a and 1102b. The holes 1116 may also be used for attachment of wire and half pin fixation elements (bolts), additional threaded or telescopic connection rods, plates, posts or other device connection elements to the first fixator ring 1102a. The second fixator ring 1102b can be identical or similar to the first fixator ring 1102a.

Although the shape of the fixator rings 1102a and 1102b as shown FIG. 13 is substantially circular, the shape of the fixator rings 1102a and 1102b can vary to accommodate the physical contour of various body parts to which the fixation system 1100 would be attached. For example, the fixator rings 1102a and 1102b can be fixator base elements configured to have an oval shape, D-shape, U-shape, C-shape, a polygon, or other irregular shapes. In some exemplary embodiments, an elliptical fixator ring (not shown) may be particularly advantageous. The insertion of pins or wires into a patient's limb can cause the surrounding tissue to swell unevenly, and in such a case, an elliptical fixator ring can accommodate the uneven swelling better than a circular ring can. The fixator rings 1102a and 1102b may be fixator base elements that form a complete ring (full ring) or a segment or portion of a ring (e.g., half ring, ⅓ ring, ¼ ring, ⅜ ring, ⅝ ring, ⅔ ring, ¾ ring, and other) that is either used alone or joined with other segments or portions of the ring to form a fixator ring (not shown). The fixator rings 1102a and 1102b may be fixator base elements constructed of any material that provides the structural rigidity necessary for fixation such as metal, alloy, carbon fiber, plastic, ceramic and so forth.

The strut 906 includes a first joint 922 and a second joint 924 connected by a center portion 926. The first joint 922 and second joint 924 are embodiments of multiple axis joints, such as the fourth, fifth, or sixth embodiment joints 600, 700, and 800, that include a generally vertical driven element. The first joint 922 includes a first driven element 928 that connects to one of the holes 916 of the first fixator ring 902a. As discussed herein, the driven element 928 can be angularly and/or rotationally repositioned relative to the center portion 926 of the strut 906. The second joint 924 includes a second driven element 930 that connects to one of the holes 916 of the second fixator ring 902b. As discussed herein, the driven element 930 can be angularly and/or rotationally repositioned relative to the center portion 926 of the strut 906. The connection strut 908 also includes first and second joints 922 and 924 and can be identical to the first connection strut 906.

The joints 922 and 924 of the struts 906 and 908 can be manipulated, for example by hand or using a tool such as a wrench, to angulate and/or rotate (depending on the joint) the driven elements 928 and 930. For example, the joints 922 and 924 can include set screws or the like on the housings thereof for allowing insertion of a wrench, screwdriver, or other such tool so that the user can drive the gears/gear assemblies (such as gears 312, 314, 414, and 514 and/or gear assemblies 616, 618, 716, 736, 802, and 804) and thereby reposition the driven elements 928 and 930.

The center portion 926 can be a strut body such as center portion 126 of the fixator assembly 200 shown in FIG. 2, which includes various adjustable elements in order to allow for six degrees of freedom. Combining two of the multiple-axis joints described herein with such a strut body can allow for effectively moving two bone segments, fixator base elements, or other elements through all six degrees of freedom.

The two struts 906 and 908 can thus be used with a set of rings 1102a and 1102b in order to move two bone segments relative to one another. First, the rings 1102a and 1102b would be attached to the bone segments with fixation elements such as half pins or k-wires. Second, the two struts 906 and 908 would be unlocked and attached to the rings 1102a and 1102b with an angular separation preferably greater than 90 degrees and an acute adjustment would be made, if necessary. Third, the struts 906 and 908 would be locked to hold the bone segments in place. Fourth, the passive struts 1130 and 1132 would be attached between the two rings 1102a and 1102b for additional support against tissue and other forces. Next, gradual adjustments could be made by unlocking the passive struts 1130 and 1132, adjusting the driven elements 928 and 930 of the active struts 906 and 908, and then once again locking the passive struts 1130 and 1132. This gradual adjustment over time could move two bone segments relative to each other in all six degrees of freedom. The passive struts 1130 and 1132 are removable such that during x-rays or other scenarios when increased access or visibility is necessary the passive struts 1130 and 1132 can be removed, and the active struts 906 and 908 are sufficient for rigidly maintaining the relative positions of the rings 1102a and 1102b.

Figure 14A:
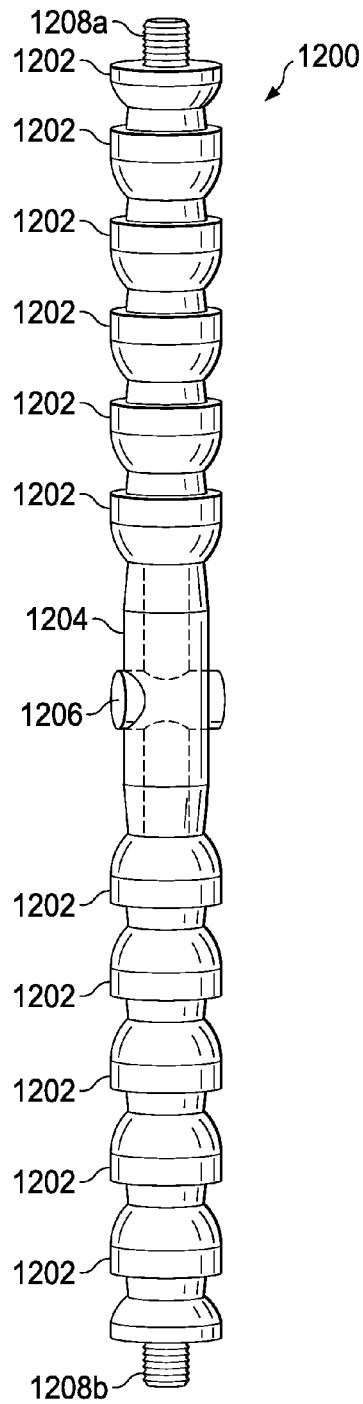
FIG. 14A is a perspective view of an embodiment of a passive support strut that can be used with external fixator ring systems of the present disclosure.
Figure 14B:
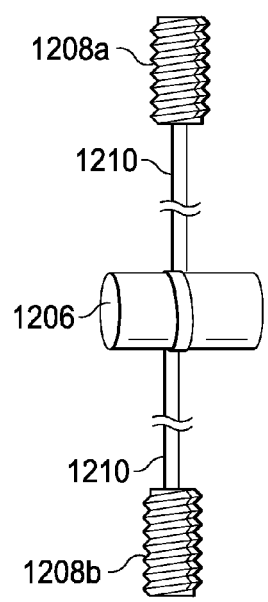
FIG. 14B is a perspective view of internal elements of the passive support strut shown in FIG. 14A.
Figure 14C:
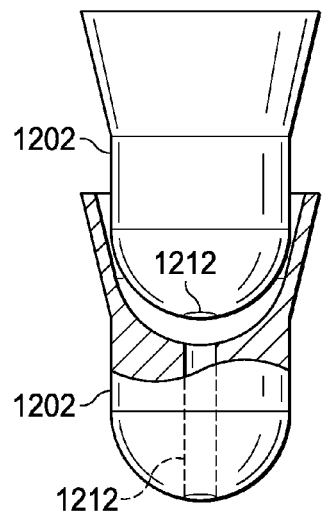
FIG. 14C is an partially-sectioned view of elements of the passive support strut shown in FIG. 14B.

FIGS. 14A through 14C show an embodiment of a passive support strut 1200 that can be used as passive struts 108 and 110 in FIG. 1, and passive struts 1132 and/or 1130 in FIG. 13. The passive support strut 1200 includes multiple joint members 1202 that are nested within one another, as shown in FIG. 14C, between a pair of attachment studs 1208a and 1208b. The attachment studs 1208a and 1208b can be used to attach the passive support strut 1200 to fixator base elements or other devices. For example, the attachment studs can be threaded studs that can pass through a hole in a fixator ring and secured in place using a threaded nut. Alternatively, the attachment studs can be configured pass through a hole in a fixator ring and secured in place using a cotter pin. Still further embodiments can use any desirable type of attachment configuration.

The joint members 1202 can rotate in all three orthogonal degrees of freedom relative to each other in order to change length and direction and to follow fixator base elements as they are driven in all six degrees of freedom by one or more active struts. The passive support strut 1200 can be locked into a rigid state such that the rings 102a and 102b are fixed relative to each other, and unlocked into a free state such that acute adjustments can be made to the relative positions of the rings 102a and 102b. As shown in FIG. 14B, the attachment studs 1208a and 1208b are each connected to a central locking element 1206 by a connection element 1210 that passes through channels 1212 of the joint members 1202. The connection element 1210 can be a cable, cord, string, wire, or the like. The central locking element 1206 is disposed within a central support member 1204. Rotation of the central locking element 1206 can wind or unwind the connection element 1210, thereby increasing or decreasing the compression on the joint members 1202 between the central support member 1204 and the attachment studs 1208a and 1208b. The locking element 1206 can be a spool, cam, or other suitable device. The joint members 1202 can be compressed together by operation of the locking element 1206 on the connection element 1210 such that friction between the joint elements 1202 prohibits relative movement between the joint elements 1202. The passive stud 1200 can thus be locked. The passive stud 1200 can be unlocked by operating the locking element 1206 in order to reduce the compression between the attachment studs 1208a, 1208b and the central support member 1204. In some embodiments, the central locking element 1206 can include slots, grooves, detents, or the like for preventing the central locking element 1206 from rotating due to the compressive forces of the connection element 1210 while the passive support strut 1200 is locked. In some embodiments, the central locking element 1206 can include a handle, lever, or other such element for allowing a technician to lock/unlock the passive support strut 1200. In some embodiments, the central locking element 1210 can include a slot, key, or otherwise be configured to be operated by a removable tool.

Figure 15:
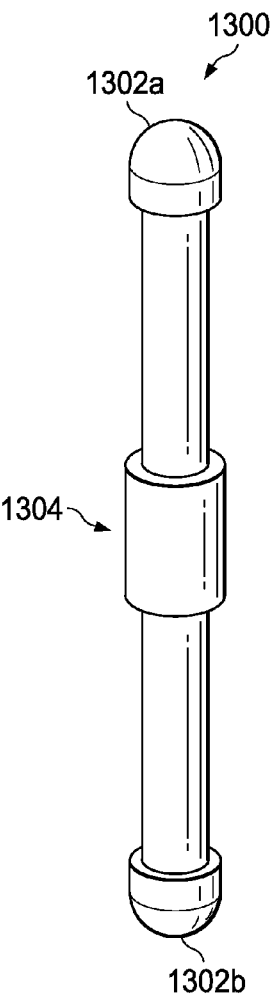
FIG. 15 is a perspective view of another embodiment of a passive support strut that can be used with external fixator ring systems of the present disclosure.

FIG. 15 shows an alternative embodiment of a support strut 1300 that can be used in place of passive struts 108 and 110 in FIG. 1, and passive struts 1132 and/or 1130 in FIG. 13. The support strut 1300 includes first and second joints 1302a and 1302b attached to opposing ends of a central portion 1304. In some embodiments, the central portion 1304 can be lengthwise adjustable. The first and second joints 1302a and 1302b can be attached to a hole in a fixator ring and secured in place using a threaded screw, bolt, combination of a nut and bolt, or any other desired attachment means. The first and second joints 1302a and 1302b can include any desired type of joint that allows for rotation in three degrees of freedom, including heim joints, universal joints, ball joints, or other joints.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:
1. A fixator system comprising:
   a first fixator base element;
   a second fixator base element;
   a first active strut connected between the first fixator base element and the second fixator base element, wherein the first active strut includes a joint comprising a driven element attached to the first fixator base element, a first drive system for rotating the driven element about a first axis of rotation, and a second drive system for rotating the driven element about a second axis of rotation, wherein the first and second axes intersect at a common point of rotation of the driven element; and a first passive strut connected between the first fixator base element and the second fixator base element;

wherein the first passive strut is configured to be placed into a passive locked state such that the first passive strut is non-adjustable and resists relative positional changes between the first and second fixator base elements, and placed into an unlocked state such that the first passive strut freely allows relative positional changes between the first and second fixator base elements;

wherein the first active strut is configured to be placed into an active locked state such that the first active strut resists relative positional changes between the first and second fixator base elements, and placed into an unlocked state such that the first active strut freely allows relative positional changes between the first and second fixator base elements; and wherein the first active strut is configured to allow for relative positional changes between the first and second fixator base elements while maintaining rigidity while the first active strut is in the active locked state.

2. The fixator system of claim 1, further comprising a second active strut connected between the first fixator base element and the second fixator base element;

wherein the second active strut is configured to be placed into an active locked state such that the second active strut resists relative positional changes between the first and second fixator base elements, and placed into an unlocked state such that the second active strut freely allows relative positional changes between the first and second fixator base elements; and wherein the second active strut is configured to allow for relative positional changes between the first and second fixator base elements while maintaining rigidity while the second active strut is in the active locked state.

3. The fixator system of claim 1, further comprising a second passive strut connected between the first fixator base element and the second fixator base element;

wherein the second passive strut is configured to be placed into a passive locked state such that the second passive strut is non-adjustable and resists relative positional changes between the first and second fixator base elements, and placed into an unlocked state such that the second passive strut freely allows relative positional changes between the first and second fixator base elements.

4. The fixator system of claim 1, wherein the joint further comprises:

a spherically-shaped element rigidly attached to the driven element such that the driven element moves with movements of the spherically-shaped element;

wherein the spherically-shaped element includes a first set of gear teeth formed in an outer surface of the spherically-shaped element and extending about at least a portion of the outer surface of the spherically-shaped element, and wherein the first drive system includes a first gear for engaging the first set of gear teeth such that rotation of the first gear causes rotation of the spherically-shaped element.

5. The fixator system of claim 4, wherein the spherically-shaped element further includes a second set of gear teeth formed in the outer surface of the spherically-shaped element and extending about at least a portion of the outer surface of the spherically-shaped element, and wherein the second drive system includes a second gear for engaging the second set of gear teeth such that rotation of the second gear causes rotation of the spherically-shaped element.

6. The fixator system of claim 5, wherein the first set of gear teeth are orthogonal to the second set of gear teeth.

7. The fixator system of claim 1, wherein the joint further comprises:

an outer spherically-shaped element; and an inner spherically-shaped element disposed within the outer spherically-shaped element and rigidly attached to the driven element such that the driven element moves with movements of the inner spherically-shaped element;

wherein the first drive system is configured for rotating the driven element about the first axis of rotation by rotating the inner spherically-shaped element about the first axis of rotation;

wherein the second drive system is configured for rotating the driven element about the second axis of rotation by rotating the outer spherically-shaped element about the second axis of rotation;

wherein the outer spherically-shaped element engages the driven element such that rotation of the outer spherically-shaped element causes angulation of the driven element and rotation of the inner spherically-shaped element about the second axis of rotation.

8. The fixator system of claim 7, wherein the inner spherically-shaped element is concentrically within the outer spherically-shaped element.

9. The fixator system of claim 1, wherein the joint further comprises:

a cylinder; and a spherically-shaped element disposed within the cylinder and rigidly attached to the driven element such that the driven element moves with movements of the spherically-shaped element;

wherein the first drive system is configured for rotating the driven element about the first axis of rotation by rotating the spherically-shaped element about the first axis of rotation;

wherein the second drive system is configured for rotating the driven element about the second axis of rotation by rotating the cylinder about the second axis of rotation; and wherein the cylinder engages the driven element such that rotation of the cylinder causes angulation of the driven element and rotation of the spherically-shaped element about the second axis of rotation.

10. The fixator system of claim 1, wherein the first passive strut comprises:

a first joint member;

a second joint member nested within the first joint member and rotatable relative to the first joint member about three orthogonal rotational axes;

a connection element passing through the first and second joint elements; and a locking element for controlling an amount of friction between the first and second joint members, thereby controlling whether the first passive strut is in the passive locked state or the unlocked state.

11. A strut for a fixator system, the strut comprising:

a first joint;

a second joint; and a central portion connected between the first and second joints, the central portion being adjustable in at least two degrees of freedom;

wherein the first joint comprises a first driven element, the first driven element being adjustable, the adjustability of the first driven element being limited to rotation about a first axis and rotation about a second axis, wherein the first and second axes intersect about a first common point of rotation of the first driven element; and wherein the second joint comprises a second driven element, the second driven element being adjustable, the adjustability of the second driven element being limited to rotation about a third axis and rotation about a fourth axis, wherein the third and fourth axes intersect about a second common point of rotation of the second driven element.

12. The strut of claim 11, wherein the first joint further comprises:
a first drive system for rotating the first driven element about the first axis; and
a second drive system for rotating the first driven element about the axis.

13. The strut of claim 11, wherein the first joint further comprises:
a spherically-shaped element rigidly attached to the first driven element such that the first driven element moves with movements of the spherically-shaped element, wherein the spherically-shaped element includes a first set of gear teeth formed in an outer surface of the spherically-shaped element and extending about at least a portion of the outer surface of the spherically-shaped element; and
a first drive system that includes a first gear for engaging the first set of gear teeth such that rotation of the first gear causes rotation of the spherically-shaped element.

14. The strut of claim 13, wherein the spherically-shaped element includes a second set of gear teeth formed in the outer surface of the spherically-shaped element and extending about at least a portion of the outer surface of the spherically-shaped element, and wherein the first joint further comprises a second drive system that includes a second gear for engaging the second set of gear teeth such that rotation of the second gear causes rotation of the spherically-shaped element.

15. The strut of claim 14, wherein the first set of gear teeth is orthogonal to the second set of gear teeth.

16. The strut of claim 13, wherein the spherically-shaped element includes a slot formed in the outer surface of the spherically-shaped element, and wherein the first joint further comprises an arm mechanism that includes an arm that extends into the slot such that movement of the arm causes rotation of the spherically-shaped element.

17. The strut of claim 13, wherein the first joint further comprises an internal joint disposed within the spherically-shaped element and a control arm attached to the spherically-shaped element via the internal joint such that rotation of the control arm causes rotation of the spherically-shaped element.

18. The strut of claim 11, wherein the joint further comprises:
an outer spherically-shaped element;
an inner spherically-shaped element disposed within the outer spherically-shaped element and rigidly attached to the first driven element such that the first driven element moves with movements of the inner spherically-shaped element;
a first drive system for rotating the first driven element about the first axis by rotating the inner spherically-shaped element about the first axis; and
a second drive system for rotating the first driven element about the second axis by rotating the outer spherically-shaped element about the second axis;
wherein the outer spherically-shaped element engages the first driven element such that rotation of the outer spherically-shaped element causes angulation of the first driven element and rotation of the inner spherically-shaped element about the second axis.

19. The strut of claim 18, wherein the inner spherically-shaped element is concentrically within the outer spherically-shaped element.

20. The strut of claim 11, wherein the joint further comprises:
a cylinder;
a spherically-shaped element disposed within the cylinder and rigidly attached to the first driven element such that the first driven element moves with movements of the spherically-shaped element;
a first drive system for rotating the first driven element about the first axis by rotating the spherically-shaped element about the first axis; and
a second drive system for rotating the first driven element about the second axis by rotating the cylinder about the second axis;
wherein the cylinder engages the first driven element such that rotation of the cylinder causes angulation of the first driven element and rotation of the spherically-shaped element about the second axis.

21. The strut of claim 20, wherein the first drive system includes:
a gear operably associated with the first driven element; and
a cylindrically cut rack having cylindrical cuts and at least one threaded end;
wherein the cylindrical cuts engage teeth of the gear such that translational motion of the cylindrically cut rack causes rotation of the gear; and
wherein the threaded end restricts translational motion of the cylindrically cut rack unless the cylindrically cut rack is rotated about a longitudinal axis of the cylindrically cut rack.

22. The strut of claim 20, wherein the first drive system includes:
a gear operably associated with the first driven element;
a rack engaged with the gear such that translational motion of the rack causes rotation of the gear;
a lead screw for supporting the rack such that rotation of the lead screw causes translational motion of the rack;
an acute adjustment block fixed relative to the lead screw such that the lead screw moves with the acute adjustment block; and
a lock member for restricting movement of the acute adjustment block when in a locked position, and for allowing movement of the acute adjustment block when in an unlocked position.

23. The strut of claim 11, wherein the central portion is lengthwise adjustable.

* * * * *